(12) United States Patent
Castro Palomino Laria et al.

(10) Patent No.: US 11,241,428 B2
(45) Date of Patent: Feb. 8, 2022

(54) HETEROARYL AMIDE DERIVATIVES AS SELECTIVE INHIBITORS OF HISTONE DEACETYLASES 1 AND/OR 2(HDAC1-2)

(71) Applicant: Medibiofarma, S.L., Noáin-Navarra (ES)

(72) Inventors: Julio Castro Palomino Laria, Barcelona (ES); Juan Camacho Gómez, Barcelona (ES); Rodolfo Rodríguez Iglesias, Noáin-Navarra (ES)

(73) Assignee: Medibiofarma, S.L., Noain-Navarra (ES)

( * ) Notice: Subject to any disclaimer, the term of this patent is extended or adjusted under 35 U.S.C. 154(b) by 26 days.

(21) Appl. No.: 16/629,457

(22) PCT Filed: Jul. 9, 2018

(86) PCT No.: PCT/ES2018/070491
§ 371 (c)(1),
(2) Date: Jan. 8, 2020

(87) PCT Pub. No.: WO2019/012172
PCT Pub. Date: Jan. 17, 2019

(65) Prior Publication Data
US 2020/0138808 A1  May 7, 2020

(30) Foreign Application Priority Data
Jul. 10, 2017 (EP) .................... 17382447

(51) Int. Cl.
*A61K 31/496* (2006.01)
*A61K 45/06* (2006.01)
*A61K 31/506* (2006.01)
*A61K 31/444* (2006.01)
*C07D 401/14* (2006.01)
*C07D 401/12* (2006.01)
*C07D 409/14* (2006.01)

(52) U.S. Cl.
CPC .......... *A61K 31/496* (2013.01); *A61K 31/444* (2013.01); *A61K 31/506* (2013.01); *A61K 45/06* (2013.01); *C07D 401/12* (2013.01); *C07D 401/14* (2013.01); *C07D 409/14* (2013.01)

(58) Field of Classification Search
CPC .... A61K 31/496; A61K 45/06; A61K 31/506; A61K 31/444; C07D 409/14; C07D 401/14; C07D 401/12
See application file for complete search history.

(56) References Cited

U.S. PATENT DOCUMENTS 9,603,950 B1   3/2017  Li et al.
2016/0137630 A1*  5/2016  Shearstone ........ A61K 31/5377
514/235.2

FOREIGN PATENT DOCUMENTS

| JP | 2009-514859 A | 4/2009 |
| JP | 2009-535333 A | 10/2009 |
| JP | 2010-531358 A | 9/2010 |
| JP | 2012-529435 A | 11/2012 |
| WO | 2016/057779 A2 | 4/2016 |
| WO | 2017/004522 A1 | 1/2017 |

OTHER PUBLICATIONS

Barton, K.M. et al., "Selective HDAC Inhibition for the Disruption of Latent HVI-1 Infection", PLOS One, vol. 9, No. 8, 2014, pp. 1-11.
Bayley, J. et al., "Skeletal Muscle Dysfunction in the db/db Mouse Model of Type 2 Diabetes", Muscle & Nerve, vol. 54, No. 3, 2016, pp. 1-9.
Cao, Y. et al., "Chemical modifier screen identifies HDAC inhibitors as suppressors of PKD models", Proceedings of the National Academy of Sciences, vol. 106, No. 51, 2009, pp. 21819-21824.
Choong, C. et al., "A novel histone deacetylase 1 and 2 isoform-specific inhibitor alleviates experimental Parkinson's disease", Neurobiology of Aging, 2015, pp. 1-54.
Fan, J. et al., "Inhibition of HDAC2 Protects the Retina from Ischemic Injury", Investigative Ophthalmology & Visual Science, vol. 54, No. 6, 2013, pp. 4072-4080.
Fischer, A. et al., "Recovery of learning and memory is associated with chromatin remodeling", Nature, vol. 447, No. 7141, 2007, pp. 178-182.

(Continued)

*Primary Examiner* — Tracy Vivlemore
*Assistant Examiner* — Ebenezer O Sackey
(74) *Attorney, Agent, or Firm* — Gary J. Gershik; Amster Rothstein & Ebenstein LLP

(57) ABSTRACT

The present invention relates to novel heteroaryl amide derivatives of formula (1)

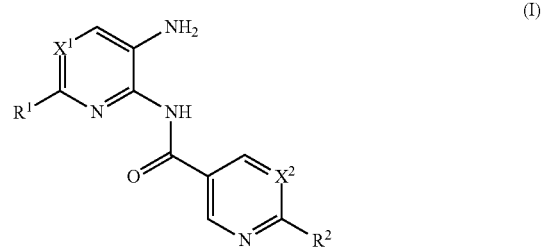

as selective inhibitors of histone deacetylase 1 and 2 (hdac1-2) to processes for their preparation, to pharmaceutical compositions comprising said compounds and to the use of said compounds for manufacturing a medicament for the treatment of pathological conditions or diseases that can improve by inhibition the activity of histone deacetylase class I, particularly HDAC1 and HDAC2, such as cancer, neurodegenerative diseases, Infectious diseases, inflammatory diseases, heart failure and cardiac hypertrophy, diabetes, polycystic kidney disease, sickle cell disease and β-thalassemia disease and to methods for the treatment of the diseases mentioned above.

23 Claims, No Drawings

(56) References Cited

OTHER PUBLICATIONS

Frumm, S.M. et al., "Selective HDAC1/HDAC2 Inhibitors Induce Neuroblastoma Differentiation", Chemistry & Biology, vol. 20, No. 5, 2013, pp. 713-725.
Glaser, K.B. et al., "Role of Class I and Class II histone deacetylases in carcinoma cells using siRNA", Biochemical and Biophysical Research Communications (BBRC), vol. 310, No. 2, 2003, pp. 529-536.
Grinshtein, N. et al., "Small molecule epigenetic screen identifies novel EZH2 and HDAC inhibitors that target glioblastoma brain tumor-initiating cells", Oncotarget, vol. 7, No. 37, 2016, pp. 59360-59376.
Holbert, M.A. and Marmorstein, R., "Structure and activity of enzymes that remove histone modifications", Current Opinion in Structural Biology, vol. 15, No. 6, 2005, pp. 673-680.
Huang, L., "Targeting Histone Deacetylases for the Treatment of Cancer and Inflammatory Diseases", Journal of Cellular Physiology, vol. 209, No. 3, 2006, pp. 611-616.
Jaworska, J. et al., "Histone deacetylases 1 and 2 are required for brain development", The International Journal of Developmental Biology, vol. 59, 2015, pp. 171-177.
Johnstone, R.W., "Histone-Deacetylase Inhibitors: Novel Drugs for the Treatment of Cancer", Nature Reviews Drug Discovery, vol. 1, No. 4, 2002, pp. 287-299.
Jung, K.H. et al., "HDAC2 Overexpression Confers Oncogenic Potential to Human Lung Cancer Cells by Deregulating Expression of Apoptosis and Cell Cycle Proteins", Journal of Cellular Biochemistry, vol. 113, No. 6, 2012, pp. 2167-2177.
Kaiser, C. and James S.R., "Acetylation of insulin receptor substrate-I is permissive for tyrosine phosphorylation", BMC Biology, vol. 2, No. 23, 2004, pp. 1-14.
Kilgore, M. et al., "Inhibitors of Class I Histone Deacetylases Reverse Contextual Memory Deficits in a Mouse Model of Alzheimer's Disease", Neuropsychopharmacology, vol. 35, No. 4, 2010, pp. 870-880.
Kobayashi, T. et al., "HDAC2 promotes loss of primary cilia in pancreatic ductal adenocarcinoma", EMBO reports, doi: 10.15252/embr.201541922, 2016, pp. 1-10.
Li, Z. et al., "Histone Deacetylase Inhibitor RGFP109 Overcomes Temozolomide Resistance by Blocking NF-κB-Dependent Transcription in Glioblastoma Cell Lines", Neurochem Res, doi: 10.1007/s11064-016-2043-5, 2016, pp. 1-14.
Lin, Z et al., "Combination of Proteasome and HDAC Inhibitors for Uterine Cervical Cancer Treatment", Clinical Cancer Research, vol. 15, No. 2, 2009, pp. 570-577.
Lkhagva, B. et al., "Novel Histone Deacetylase Inhibitor Modulates Cardiac Peroxisome Proliferator-Activated Receptors and Inflammatory Cytokines in Heart Failure", Pharmacology, vol. 96, 2015, pp. 184-191.
Marks, P.A. et al., "Histone Deacetylase Inhibitors", Advances in Cancer Research, vol. 91, 2004, pp. 137-168.
McKinsey, T.A., "Targeting Inflammation in Heart Failure with Histone Deacetylase Inhibitors", Molecular Medicine, vol. 17, No. 5, 2011, pp. 434-441.
Mottamal, M. et al., "Histone Deacetylase Inhibitors in Clinical Studies as Templates for New Anticancer Agents", Molecules, vol. 20, No. 3, 2015, pp. 3898-3941.
Nural-Guvener, H., "Anti-Fibrotic Effects of Class I HDAC Inhibitor, Mocetinostat Is Associated with IL-6/Stat3 Signaling in Ischemic Heart Failure", International Journal of Molecular Sciences, vol. 16, No. 5, pp. 11482-11499.
Quint, K. et al., "Clinical significance of histone deacetylases 1, 2, 3, and 7: HDAC2 is an independent predictor of survival in HCC", Virchows Arch, vol. 459, No. 2, 2011, pp. 129-139.
Senese, S. et al., "Role for Histone Deacetylase 1 in Human Tumor Cell Proliferation", Molecular and Cellular Biology, vol. 27, No. 13, 2007, pp. 4784-4795.
Seo, J. et al., "Expression of Histone Deacetylases HDAC1, HDAC2, HDAC3, and HDAC6 in Invasive Ductal Carcinomas of the Breast", Journal of Breast Cancer, vol. 17, No. 4, 2014, pp. 323-331.
Shearstone, J. et al., "Chemical Inhibition of Histone Deacetylases 1 anc 2 Induces Fetal Hemoglobin through Activation of GATA2", PLOS One, vol. 11, No. 4, 2016, pp. 1-27.
Stubbs, M.C. et al., "Selective Inhibition of HDAC1 and HDAC2 as a Potential Therapeutic Option for B-ALL", Clinical Cancer Research, vol. 21, No. 10, 2015, pp. 1-33.
Tan, J. et al., "Novel histone deacetylase inhibitors in clinical trials as anti-cancer agents", Journal of Hematology & Oncology, vol. 3, No. 5, 2010, pp. 1-13.
Thomas, E.A., "Involvement of HDAC1 and HDAC3 in the Pathology of Polyglutamine Disorders: Therapeutic Implications for Selective HDAC1/HDAC3 Inhibitors", Pharmaceuticals, vol. 7, No. 6, 2014, pp. 634-661.
Trivedi, C.M. et al., "Hdac2 regulates the cardiac hypertrophic response by modulating Gsk3β activity", Nature Medicine, vol. 13, No. 3, 2007, pp. 324-331.
Wagner, F.F. et al., "Kinetically selective inhibitors of histone deacetylase 2 (HDAC2) as cognition enhancers", Chemical Science, vol. 6, No. 1, 2014, pp. 804-815.
Wightman, F. et al., "Entinostat is a histone deacetylase inhibitor selective for class 1 histone deacetylases and activates HIV production from latently infected primary T cells", AIDS, vol. 27, No. 18, 2013, pp. 2853-2862.
Witt, O. et al., "HDAC family: What are the cancer relevant targets?", Cancer Letters, vol. 277, No. 1, 2009, pp. 8-21.
Woods, D.M. et al., "HDAC Inhibition Upregulates PD-1 Ligands in Melanoma and Augments Immunotherapy with PD-1 Blockade", Cancer Immunology Research, vol. 3, No. 12, 2015, pp. 1-29.
Xu, K. et al., "Targeting HDACs: A Promising Therapy for Alzheimer's Disease", Oxidative Medicine and Cellular Longevity, vol. 2011, 2011, pp. 1-5.
Yang, F. et al., "Selective class I histone deacetylase inhibitors suppress persistent spontaneous nociception and thermal hypersensitivity in a rat model of bee venom-induced inflammatory pain", Acta Physiologica Sinice, vol. 67, No. 5, 2015, pp. 447-454.
Yang, H. et al., "Overexpression of histone deacetylases in cancer cells is controlled by interplay of transcription factors and epigenetic modulators", The FASEB Journal, vol. 28, No. 10, 2014, pp. 4265-4279.
Yang, J. et al., "Inhibiting histone deacetylases suppresses glucose metabolism and hepatocellular carcinoma growth by restoring FBP1 expression", Scientific Reports, doi: 10.1038/srep43864, 2017, pp. 1-13.
Zhao, H. et al., "HDAC2 overexpression is a poor prognostic factor of breast cancer patients with increased multidrug resistance-associated protein expression who received anthracyclines therapy", Japanese Journal of Clinical Oncology, vol. 46, No. 10, 2016, pp. 1-10.
Zhao, J. et al., "Histone deacetylases 1 and 2 cooperate in regulating BRCA1, CHK1, and RAD51 expression in acute myeloid leukemia cells", Oncotarget, vol. 8, No. 4, 2017, pp. 6319-6329.
Office Action dated Oct. 19, 2021 in connection with Japanese Application No. 2020-523052 (English translation).
Bressi, J.C. et al., "Exploration of the HDAC2 foot pocket; Synthesis and SAR of subsitiutued N-(2-aminophenyl) benzamides", Bioorganic & Medicinal Chemistry Letters, 2010, vol. 20, pp. 3142-3145.
Methot, J.L. et al., "Exploration of the internal cavity of histone deacetylase (HDAC) with selective HDAC1/HDAC2 inhibitors (SHI-1:2)", Bioorganic & Medicinal Chemistry Letters, 2008, vol. 18, pp. 973-978.

\* cited by examiner

HETEROARYL AMIDE DERIVATIVES AS SELECTIVE INHIBITORS OF HISTONE DEACETYLASES 1 AND/OR 2(HDAC1-2)

RELATED APPLICATIONS

This application is a § 371 national stage of PCT International Application No. PCT/ES2018/070491, filed Jul. 9, 2018, claiming priority of European Patent Application No. 17382447.5, filed Jul. 10, 2017, the contents of each of which are hereby incorporated by reference into this application.

FIELD OF THE INVENTION

The present invention relates to novel heteroaryl amide derivatives as selective inhibitors of at least one enzyme histone deacetylase class I selected from HDAC1 and HDAC2.

Other objectives of the present invention are to provide a procedure for preparing these compounds; pharmaceutical compositions comprising an effective amount of these compounds; the compounds for use in the treatment of pathological conditions, disorder or diseases that can improve by inhibition the activity of at least one enzyme histone deacetylase class I, selected from HDAC1 and HDAC2, such as cancer, neurodegenerative diseases, Infectious diseases, inflammatory diseases, heart failure and cardiac hypertrophy, diabetes, polycystic kidney disease, sickle cell disease and 3-thalassemia disease.

STATE OF THE ART

Histone deacetylases (HDACs) catalyse the removal of acetyl groups from histones, proteins that organize and modulate the structure of chromatin in nucleosomes. HDAC-mediated deacetylation of chromatin-bound histones regulates the expression of a variety of genes throughout the genome. Importantly, HDACs have been linked to cancer, as well as other health conditions.

At least 18 HDAC subtypes exist and they are subdivided into three families of HDACs: class I (HDACs 1, 2, 3, and 8) and class II (HDACs 4, 5, 6, 7, 9, and 10) HDACs are zinc-dependent amidohydrolases with a conserved catalytic core but differing in size, domain structure, tissue expression pattern and cellular localization (Johnstone, Ricky W. *Histone-deacetylase inhibitors: novel drugs for the treatment of cancer*. Nature reviews Drug discovery, 2002, vol. 1, no 4, p. 287-299). Another HDAC, HDAC11, lies at the boundary between the two classes. Class III HDACs (Sirtuins 1-7) are $NAD^+$-dependent and unrelated in sequence to classes I and II (HOLBERT, Marc A.; MARMORSTEIN, Ronen. *Structure and activity of enzymes that remove histone modifications*. Current opinion in structural biology, 2005, vol. 15, no 6, p. 673-680).

As a regulator of the common post-translational modification of protein acetylation, the zinc-dependent histone deacetylases (Class I and II HDAC) play a critical role in diverse cellular processes. The family of zinc-dependent histone deacetylases has been variously implicated in different disease states. Zinc-dependent HDACs have received much attention as anticancer drug targets. Inhibitors of these enzymes show a remarkable ability to induce terminal differentiation of transformed cells, presumably by altering patterns of gene expression through influencing the acetylation state of selected histone lysine residues (MARKS, Paul A., et al. *Histone deacetylase inhibitors*. Advances in cancer research, 2004, vol. 91, p. 137-168).

However, it is known that HDACs forms multiprotein complexes with many regulatory proteins inside the cell. Each isozyme interacts with a specific series of regulatory proteins and transcription factors and has a specific set of substrates, and thus each regulates a specific series of genes and proteins (WITT, Olaf, et al. HDAC family: What are the cancer relevant targets?. Cancer letters, 2009, vol. 277, no 1, p. 8-21).

HDAC1/HDAC2 and Cancer

In contrast to other class I enzymes, HDAC1 and HDAC2 are emerging therapeutic targets for the treatment of cancer and other diseases. (HUANG, Lili. *Targeting histone deacetylases for the treatment of cancer and inflammatory diseases*. Journal of cellular physiology, 2006, vol. 209, no 3, p. 611-616). RNAi-mediated knockdown of HDAC1 expression inhibits proliferation and, importantly, induces apoptosis in several tumor cell lines in vitro (GLASER, Keith B., et al. Role of class I and class II histone deacetylases in carcinoma cells using siRNA. Biochemical and biophysical research communications, 2003, vol. 310, no 2, p. 529-536).

Likewise, it has been shown that in the absence of HDAC1 cells can arrest either at the G1 phase of the cell cycle or at the G2/M transition, resulting in the loss of mitotic cells, cell growth inhibition, and an increase in the percentage of apoptotic cells. (SENESE, Silvia, et al. *Role for histone deacetylase 1 in human tumor cell proliferation*. Molecular and cellular biology, 2007, vol. 27, no 13, p. 4784-4795).

In addition, it is also known that in colon cancer cells HDAC1 and HDAC2 are overexpressed, in this case the interactions among transcription factors and epigenetic modulators orchestrate the activation of HDAC1 and HDAC2 promoter activity in said cells. (YANG, Hui, et al. *Overexpression of histone deacetylases in cancer cells is controlled by interplay of transcription factors and epigenetic modulators*. The FASEB Journal, 2014, vol. 28, no 10, p. 4265-4279).

It has been demonstrated that selective HDAC1/HDAC2 inhibition using compounds or RNA interference induced differentiation and decreased viability in neuroblastoma cell lines. (FRUMM, Stacey M., et al. *Selective HDAC1/HDAC2 inhibitors induce neuroblastoma differentiation*. Chemistry & biology, 2013, vol. 20, no 5, p. 713-725).

Recently, studies disclosed that inhibition or silencing of histone deacetylase 2 (HDAC2) restores primary cilia formation in pancreatic ductal adenocarcinoma (PDAC) cells. Loss of primary cilia is frequently observed in tumor cells, including PDAC cells, suggesting that the absence of this organelle may promote tumorigenesis through aberrant signal transduction and the inability to exit the cell cycle. Inactivation of HDAC2 results in decreased Aurora A expression, which promotes disassembly of primary cilia. According these studies HDAC2, controls ciliogenesis independently of Kras, which facilitates Aurora A expression, suggesting that HDAC2 is a novel regulator of primary cilium formation in PDAC cells. (KOBAYASHI, Tetsuo, et al. *HDAC2 promotes loss of primary cilia in pancreatic ductal adenocarcinoma*. EMBO reports, 2016, p. e201541922).

On the other hand, it has been demonstrated that HDAC1/HDAC2 inhibitors are a potential therapeutic option for B-cell acute lymphoblastic leukemia (B-ALL), and that specific inhibitor could be therapeutically useful for patients with B-ALL. (STUBBS, Matthew C., et al. Selective Inhibition of HDAC1 and HDAC2 as a Potential Therapeutic Option for B-ALL. Clinical Cancer Research, 2015, vol. 21, no 10, p. 2348-2358).

Regarding Central Nervous System (CNS) tumors, specifically brain and spinal cord tumors, it is known that Blood-brain barrier (BBB) penetration is one of the major issues impeding successful therapeutic targeting in glioblastoma (GBM), as more than 98% of drugs fail to cross the BBB. In this sense, it has been reported class I HDAC inhibitor, specifically HDAC1/HDAC2 inhibitor that crossed the BBB. This inhibitor exhibited cytotoxicity in vitro on a panel of brain-tumor initiating cell lines (BTIC lines) and extended survival in combination with an alkylating agent temozolomide (TMZ) in an orthotopic BTIC model in vivo. (GRINSHTEIN, Natalie, et al. *Small molecule epigenetic screen identifies novel EZH2 and HDAC inhibitors that target glioblastoma brain tumor-initiating cells*. Oncotarget, 2016, vol. 7, no 37, p. 59360-59376).

Other studies have pointed out of that selective histone deacetylase class I inhibitors overcomes Temozolomide resistance and downregulates the expression of NF-κB-regulated pro-survival genes in a temozolomide-resistant glioblastoma cell line. (Zong-yang Li, et al, *Histone Deacetylase Inhibitor RGFP109 Overcomes Temozolomide Resistance by Blocking NF-κB-Dependent Transcription in Glioblastoma Cell Lines*, Neurochem Res, September 2016, DOI 10.1007/s11064-016-2043-5).

There are studies demonstrating inhibition of both HDAC1 and HDAC2 is necessary to decrease the expression of BRCA1, CHK1, and RAD51, enhance cytarabine- or daunorubicin-induced DNA damage and apoptosis, and abrogate cytarabine- or daunorubicin-induced cell cycle checkpoint activation in acute myeloid leukemia (AML) cells. (ZHAO, J., et al. Histone deacetylases 1 and 2 cooperate in regulating BRCA1, CHK1, and RAD51 expression in acute myeloid leukemia cells. Oncotarget, 2016l.

Histone deacetylase 2 (HDAC2) is crucial for embryonic development, affects cytokine signaling relevant for immune responses, and is often significantly overexpressed in solid tumors. Specifically, in lung cancer it has been demonstrated the aberrant expression of HDAC2, and its inactivation resulted in regression of tumor cell growth and activation of cellular apoptosis via p53 and Bax activation and Bcl2 suppression. (JUNG, Kwang Hwa, et al. *HDAC2 overexpression confers oncogenic potential to human lung cancer cells by deregulating expression of apoptosis and cell cycle proteins*. Journal of cellular biochemistry, 2012, vol. 113, no 6, p. 2167-2177).

On the other hand, studies have demonstrated the elevated HDAC1/HDAC2 expression in cervical dysplasia and cervical carcinoma versus normal uterine cervical epithelium. In said studies bortezomib and HDAC inhibitor were combined and showed synergistic killing of HPV-positive, but not HPV-negative, cervical cancer cell lines. Similarly, treatment of HeLa xenografts with the combination of bortezomib and HDAC1/HDAC2 inhibitor retarded tumor growth significantly more effectively than either bortezomib agent alone, suggesting that combination treatment of HDAC inhibitors with bortezomib, warrants exploration for the treatment of cervical cancer. (LIN, Zhenhua, et al. *Combination of proteasome and HDAC inhibitors for uterine cervical cancer treatment*. Clinical Cancer Research, 2009, vol. 15, no 2, p. 570-577.)

Other studies have linked HDACs 1 and HDAC2 expressions in hepatocellular carcinoma (HCC) and their correlation with clinical data and patient survival. Said studies demonstrated that HDAC1 and HDAC2 were expressed significantly higher in cancer cells compared to normal tissue. Specifically, high HDAC2 expression was associated with poor survival in low-grade and early-stage tumors ($p<0.05$) suggesting that HDAC2 expression had an impact on patient survival. (QUINT, Karl, et al. *Clinical significance of histone deacetylases 1, 2, 3, and 7: HDAC2 is an independent predictor of survival in HCC*. Virchows Archiv, 2011, vol. 459, no 2, p. 129-139). Additionally, it has been found that low expression of fructose-1,6-bisphosphatase (FBP1) correlated with high levels of HDAC1 and HDAC2 proteins in hepatocellular carcinoma (HCC) patient tissues. Treatment of HCC cells with HDAC inhibitors or knockdown of HDAC1 and/or HDAC2 restored FBP1 expression and inhibited HCC cell growth. (Yang J, et al. *Inhibiting histone deacetylases suppresses glucose metabolism and hepatocellular carcinoma growth by restoring FBP1 expression*. Sci Rep. 2017 Mar. 6; 7:43864).

HDAC2 overexpression has been correlated with the metastasis, progression and the increased multidrug resistance protein expression in breast cancer, suggesting that HDAC2 could be a prognostic factor of breast cancer patients, especially the patients who received anthracyclines therapy (ZHAO, Haishan, et al. *HDAC2 overexpression is a poor prognostic factor of breast cancer patients with increased multidrug resistance-associated protein expression who received anthracyclines therapy*. Japanese journal of clinical oncology, 2016).

At the same time, HDAC1 expression was significantly correlated with the molecular subtypes of tumors, with the highest expression being observed in luminal tumors in invasive ductal carcinomas of the breast (SEO, Jinwon, et al. *Expression of histone deacetylases HDAC1, HDAC2, HDAC3, and HDAC6 in invasive ductal carcinomas of the breast*. Journal of breast cancer, 2014, vol. 17, no 4, p. 323-331).

Several evidences for the involvement of HDAC1 and HDAC2 in cancer suggest that inhibitors selective for these subtypes may demonstrate an improved therapeutic index through enhanced clinical efficacy and/or better tolerability compared to pan HDAC inhibitors.

HDAC1/HDAC2 and Neurodegenerative Diseases

A significant amount of data implicates HDACs in diverse biological processes. In line with this, studies have shown that class I HDAC play an essential role in nervous system development.

Regarding the above, treatment with HDAC inhibitors have shown to ameliorate cognitive deficits in genetic models of neurodegenerative disease (FISCHER, Andre, et al. *Recovery of learning and memory is associated with chromatin remodeling*. Nature, 2007, vol. 447, no 7141, p. 178-182) and also they have been used for treating the cognitive deficits associated with early stage of Alzheimer's disease (AD)(KILGORE, Mark, et al. *Inhibitors of class 1 histone deacetylases reverse contextual memory deficits in a mouse model of Alzheimer's disease*. Neuropsychopharmacology, 2010, vol. 35, no 4, p. 870-880). These studies suggest that modulating memory via HDAC inhibition have considerable therapeutic potential for many memory and cognitive disorders.

Emerging literature now positions class I HDACS, specifically HDAC1 and HDAC2, as important control points in brain development. The highly homologous HDAC1 and HDAC2 are detected at different stages of neuronal commitment and differentiation during central nervous system age-dependent evolution. This implicates their contribution to the regulation of the developmentally specific gene expression and to the maintenance of the central nervous system CNS. These processes appear to be particularly sensitive to disruption in epigenetic gene regulation, leading among others to syndromes associated with mental retardation as well as complex psychiatric disorders. Expression of HDAC1 and HDAC2 during brain development and the involvement of HDAC1 and HDAC2 in neurogenesis have been extensively demonstrated through conducted studies. (ZIEMKA-NALECZ, Malgorzata; JAWORSKA, Joanna; ZALEWSKA, Teresa. *Histone deacetylases 1 and 2 are required for brain development*. International Journal of Developmental Biology, 2015, vol. 59, no 4-5-6, p. 171-177; and references therein).

Likewise, other studies have demonstrated that selective pharmacological inhibition of HDAC2 is feasible and that inhibition of the catalytic activity of this enzyme may serve as a therapeutic approach towards enhancing the learning and memory processes that are affected in many neurological and psychiatric disorders (WAGNER, F. F., et al. *Kinetically selective inhibitors of histone deacetylase 2 (HDAC2) as cognition enhancers*. Chemical science, 2015, vol. 6, no 1, p. 804-8159). Thus, it has been shown that HDAC2 regulates memory processes and as such are interesting target for memory enhancement or extinction in memory affecting condition such as, but not limited to Alzheimer's disease, post-traumatic stress disorder or drug addiction. (XU, Ke, et al. *Targeting HDACs: a promising therapy for Alzheimer's disease*. Oxidative medicine and cellular longevity, 2011, vol. 2011).

Besides that, other studies have disclosed the involvement of HDAC1 in polyglutamine disorders, including Huntington's disease, and the use of HDAC1-selective inhibitors as therapeutic intervention for these disorders (THOMAS, Elizabeth A. *Involvement of HDAC1 and HDAC3 in the pathology of polyglutamine disorders: therapeutic implications for selective HDAC1/HDAC3 inhibitors*. Pharmaceuticals, 2014, vol. 7, no 6, p. 634-661).

Similarly, it has been identified HDAC1-2 isoform-specific inhibitor with protective effects against MPP+/MPTP-induced neuronal death in both in vitro and in vivo Parkinson's disease (PD) model, suggesting that selective inhibition of HDAC1 and 2 may pave the way to new strategies for PD treatment (CHOONG, Chi-Jing, et al. *A novel histone deacetylase 1 and 2 isoform-specific inhibitor alleviates experimental Parkinson's disease*. Neurobiology of aging, 2016, vol. 37, p. 103-116).

HDAC1/HDAC2 and Inflammatory Diseases

Studies have shown new line of evidence showing involvement of epigenetic regulation of chromatin structure by HDAC1/2-mediated histone hypoacetylation in the bee venom (BV)-induced persistent spontaneous nociception (PSN) and thermal hypersensitivity and demonstrate the beneficial effects of these class I HDACi in prevention of peripheral inflammatory pain from occurring. (YANG, F., et al. *Selective class I histone deacetylase inhibitors suppress persistent spontaneous nociception and thermal hypersensitivity in a rat model of bee venom-induced inflammatory pain*, Acta physiologica Sinica, 2015, vol. 67, no 5, p. 447-454).

On the other hands, studies have demonstrated the expression of higher levels of HDAC1 and HDAC2 in left ventricles (LVs) of Heart failure (HF) rats. This study suggests that HDAC inhibition can improve cardiac function and attenuate the effects of heart failure (HF) on cardiac metabolism and inflammation (LKHAGVA, Baigalmaa, et al. *Novel histone deacetylase inhibitor modulates cardiac peroxisome proliferator-activated receptors and inflammatory cytokines in heart failure*. Pharmacology, 2015, vol. 96, no 3-4, p. 184-191).

Protein acetylation is an essential mechanism in regulating transcriptional and inflammatory events. Studies have shown that nonselective histone deacetylase inhibitors can protect the retina from ischemic injury in rats. This study has demonstrated that suppressing HDAC2 expression can effectively reduce ischemic retinal injury, suggesting that the development of selective HDAC2 inhibitors may provide an efficacious treatment for ischemic retinal injury. (FAN, Jie, et al. *Inhibition of HDAC2 Protects the Retina From Ischemic Injury Inhibition of HDAC2 Protects Retina From Ischemic Injury*. Investigative ophthalmology & visual science, 2013, vol. 54, no 6, p. 4072-4080).

HDAC1/HDAC2 and Heart Failure

HDAC2 has been identified as an important molecular target in the heart, and joint to Gsk3beta, are considered components of a regulatory pathway providing an attractive therapeutic target for the treatment of cardiac hypertrophy and heart failure (TRIVEDI, Chinmay M., et al. *Hdac2 regulates the cardiac hypertrophic response by modulating Gsk3βactivity*. Nature medicine, 2007, vol. 13, no 3, p. 324-331).

The induction of Hsp70 in response to diverse hypertrophic stresses and the ensuing activation of HDAC2 trigger cardiac hypertrophy, emphasizing HSP70/HDAC2 as a novel mechanism regulating hypertrophy (MCKINSEY, Timothy A. *Targeting inflammation in heart failure with histone deacetylase inhibitors*. Molecular medicine, 2011, vol. 17, no 5, p. 434).

In vivo treatment of congestive heart failure (CHF) animals with Mocetinostat reduced CHF-dependent up-regulation of HDAC1 and HDAC2 in CHF myocardium, improved cardiac function and decreased scar size and total collagen amount, demonstrating an in vivo regulation of cardiac fibroblasts via HDAC1-2 inhibition (NURAL-GUVENER, Hikmet, et al. *Anti-fibrotic effects of class I HDAC inhibitor, mocetinostat is associated with IL-6/Stat3 signalling in ischemic heart failure*. International journal of molecular sciences, 2015, vol. 16, no 5, p. 11482-11499).

HDAC1/HDAC2 in Other Diseases

Recent reports indicate that HDAC2 has been reported to bind with IRS-1 in liver cells of the diabetes db/db mouse. These mice have been routinely used for screening various insulin mimetics as well as insulin sensitizers (BAYLEY, Jeppe Seamus; PEDERSEN, Thomas Holm; NIELSEN, Ole Baekgaard. *Skeletal muscle dysfunction in the db/db mouse model of type 2 diabetes*. Muscle & nerve, 2016, vol. 54, no 3, p. 460-468). This binding of HDAC2 with IRS-1 leads to decreased acetylation and reduced insulin receptor-mediated tyrosine phosphorylation of IRS-1. Accordingly, the HDAC inhibitor Trichostatin A (TSA) or gene silencing of HDAC2 enhance acetylation of IRS-1 and partially attenuate insulin resistance (C. Kaiser, S. R. James, *Acetylation of insulin receptor substrate*-1 *is permissive for tyrosine phosphorylation*, BMC Biol. 2 (2004) 23).

On the other hand, selective histone deacetylase (HDAC) inhibitors have emerged as a potential anti-latency therapy for persistent human immunodeficiency virus type 1 (HIV-1) infection. (BARTON, Kirston M., et al. *Selective HDAC inhibition for the disruption of latent HIV-1 infection*. PloS one, 2014, vol. 9, no 8, p. e102684). Specifically, HDAC inhibitor entinostat, selective for inhibition of class I HDACs, induced virus expression in latently infected primary CD4[+] T cells making this compound an attractive novel option for future clinical trials. (WIGHTMAN, Fiona, et al. *Entinostat is a histone deacetylase inhibitor selective for class 1 histone deacetylases and activates HIV production from latently infected primary T cells.* AIDS (London, England), 2013, vol. 27, no 18, p. 2853).

Other studies have reveal a critical role for HDAC1 in polycystic kidney disease (PKD) pathogenesis and point to HDAC inhibitors as drug candidates for PKD treatment. Said studies demonstrated that inhibiting class I HDACs, by knocking down HDAC1, suppressed kidney cyst formation and body curvature caused by pkd2 deficiency. (CAO, Ying, et al. *Chemical modifier screen identifies HDAC inhibitors as suppressors of PKD models.* Proceedings of the National Academy of Sciences, 2009, vol. 106, no 51, p. 21819-21824).

It is known that chemical inhibition of HDAC1/HDAC2 induces fetal hemoglobin (HBF) through activation of GATA2. Therapeutic intervention aimed at reactivation of fetal hemoglobin protein (HbF) is a promising approach for ameliorating sickle cell disease (SCD) and β-thalassemia. Studies have shown genetic knockdown of histone deacetylase 1 or 2 is sufficient to induce HbF. (SHEARSTONE, Jeffrey R., et al. *Chemical Inhibition of Histone Deacetylases 1 and 2 Induces Fetal Hemoglobin through Activation of GATA2*. PloS one, 2016, vol. 11, no 4, p. e0153767).

Finally, it has been demonstrated that class I HDAC inhibitors upregulated the expression of PD-L1 and, to a lesser extent, PD-L2 in melanomas. HDAC inhibitor treatment resulted in rapid upregulation of histone acetylation of the PDL1 gene leading to enhanced and durable gene expression. Said upregulation of PD-L1 was confined to inhibition of the class I HDAC, specifically HDAC1 and HDAC2. The efficacy of combining HDAC inhibition with PD-1 blockade for treatment of melanoma was explored in a murine B16F10 model. The results highlight the ability of epigenetic modifiers to augment immunotherapies, providing a rationale for combining HDAC inhibitors with PD-1 blockade (WOODS, David M., et al. *HDAC inhibition upregulates PD-1 ligands in melanoma and augments immunotherapy with PD-1 blockade.* Cancer immunology research, 2015, vol. 3, no 12, p. 1375-1385).

HDAC Inhibitors

Several inhibitors of histone deacetylases have been developed and approved as treatment of human disease, specifically as anti-cancer agents, such as: vorinostat (cutaneous T cell lymphoma and multiple myeloma), romidepsin (peripheral T-cell lymphoma), and belinostat (peripheral T-cell lymphoma) (TAN, Jiahuai, et al. *Novel histone deacetylase inhibitors in clinical trials as anti-cancer agents*. Journal of hematology & oncology, 2010, vol. 3, no 1, p. 5). Even though these inhibitors are approved for cutaneous and/or peripheral T-cell lymphoma, these drugs are still being studied in clinical trials for other types of cancers, either as single agents or in combination with other drugs, and other HDAC inhibitors are in different stages of clinical trials for various haematological and solid tumours.

Besides the promising effects on anticancer activities, the use of HDAC inhibitors in other diseases, such as intestinal fibrosis, autoimmune, inflammatory diseases, metabolic disorders and many more, is also growing.

However, HDAC inhibitors are also associated with toxicities. The most common grade 3 and 4 adverse events observed with the use of HDAC inhibitors were thrombocytopenia, neutropenia, anemia, fatigue and diarrhea (MOTTAMAL, Madhusoodanan, et al. *Histone deacetylase inhibitors in clinical studies as templates for new anticancer agents*. Molecules, 2015, vol. 20, no 3, p. 3898-39419).

Known HDAC inhibitors fail to show prominent HDAC isozyme selectivity. This fact could be a cause of serious problems in a clinical setting, especially in the treatment of diseases and conditions wherein a prolonged drug administration is required. Therefore, the design of selective HDAC inhibitors allows preferential inhibition of only the isozyme(s) relevant to a particular disease or condition, thereby reducing the probability of counterproductive and/or adverse effects and to minimize the cytotoxic effects in patients, resulting from an unwanted and undesired inhibition of other HDAC isozymes. It is therefore, desirable to develop new isoform-selective HDAC inhibitors offering more efficacy and less toxicity in patients.

There remains a need for providing HDAC inhibitors, particularly potent and/or selective inhibitors of particular classes of HDACs.

Therefore, the problem to be solved by the present invention is to provide new compounds as inhibitors of histone deacetylase class I, and more particularly as selective inhibitors of histone deacetylase selective from HDAC1 and HDAC2.

The authors of the present invention have developed new N-(3-aminopyridin-2-yl) nicotinamide derivatives conveniently substituted as potent and selective inhibitors of HDAC1 and/or HDAC2.

SUMMARY OF THE INVENTION

In one of its aspects (aspect 1), the present invention refers to heteroaryl amide derivatives of formula (I):

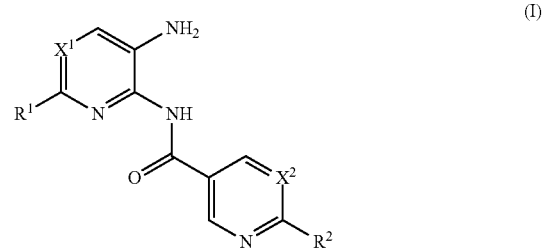

Wherein:
$X^1$ and $X^2$ represent independently a group selected from —CH and N;
$R^1$ represents:
a) phenyl group optionally substituted by one or more substituents selected from the group consisting of halogen atom, linear or branched $C_1$-$C_4$ haloalkyl group, and linear or branched $C_1$-$C_4$ alkoxy,
b) five or a six-membered heteroaryl ring optionally substituted by one or more substituents selected from the group consisting of halogen atom, linear or branched $C_1$-$C_4$ alkoxy, cyano group, linear or branched $C_1$-$C_4$ haloalkyl, linear or branched $C_1$-$C_4$ alkyl, $C_3$-$C_6$ cycloalkyl, $C_3$-$C_6$ cycloalkoxy and $C_5$-$C_6$ heterocyclic ring optionally substituted by one or more halogen atoms;
$R^2$ represents a group selected from:
a) —N($R^3$)($R^4$) group, wherein:
  1-$R^3$ and $R^4$ form together with the nitrogen atom to which they are bound a five or six-membered saturated cycle comprising optionally an additional heteroatom as part of the cycle selected from N and O, which is optionally substituted by a $C_1$-$C_3$ alkyl group or an —N($R^5$)($R^6$) group, wherein $R^5$ and $R^6$ form together with the nitrogen atom to which they are bound a five or six-membered saturated cycle comprising optionally an additional heteroatom as part of the cycle selected from N and O, which is optionally substituted by a $C_1$-$C_3$ alkyl group, or 2-$R^3$ and $R^4$ represent independently a group selected from hydrogen atom, $C_3$-$C_6$ cycloalkyl group and linear or branched $C_1$-$C_3$ alkyl, which is optionally substituted by a five or six-membered heterocycle comprising one or two heteroatoms selected from N and O as part of the cycle, which is optionally substituted by linear or branched $C_1$-$C_3$ alkyl group.

b) phenyl ring optionally substituted by one or more substituent selected from halogen atoms and cyano group, c) $C_3$-$C_6$ cycloalkyl optionally substituted by one or more substituent selected from linear or branched $C_1$-$C_3$ alkyl and hydroxy group, d) $C_5$-$C_6$ heteroaryl optionally substituted by a group selected from halogen atom, linear or branched $C_1$-$C_3$ alkyl and linear or branched $C_1$-$C_3$alkoxy and —N($R^5$)($R^6$) group wherein $R^5$ and $R^6$ form together with the nitrogen atom to which they are bound a five or six-membered saturated cycle comprising optionally an additional heteroatom selected from N and O as part of the cycle and which is optionally substituted by a $C_1$-$C_3$ alkyl group, e) Hydrogen atom, and pharmaceutically acceptable salts thereof.

Other aspects of the present invention are:

Aspect 2) processes for the preparation of the compounds of aspect 1.

Aspect 3) pharmaceutical compositions comprising an effective amount of a compound of aspect 1.

Aspect 4) pharmaceutical compositions according to aspect 3 further comprising a therapeutically effective amount of one or more therapeutic agents selected from the group consisting of chemotherapeutics agents, anti-inflammatory agents, steroids, immunosuppressants, therapeutic antibodies and adenosine antagonist.

Aspect 5) Compounds as defined in aspect 1 for used in the treatment of diseases or pathological conditions that can be ameliorated by inhibition of histone deacetylase class I, specifically HDAC1 and HDAC2.

Aspect 6) methods for the treatment of diseases that can be ameliorated by inhibition of histone deacetylase class I, selected from HDAC1 and HDAC2 by administration of the compounds of aspect 1 or the pharmaceutical compositions of aspect 3 or 4 to a subject in need of said treatment where said diseases may be selected from cancer selected from colon, lung, breast, central nervous system (CNS) cancer, uterine cervical cancer, pancreatic adenocarcinoma, hepatocellular carcinoma, gastric cancer, tissue cancer and T-cell malignances selected from acute myeloid leukemia, acute lymphoblastic leukemia, cutaneous T-cell lymphoma, peripheral T-cell lymphoma, B-cell lymphoma and multiple myeloma; neurodegenerative diseases selected from Alzheimer's disease, post-traumatic stress disorder, drug addiction, Parkinson's disease, Huntington's disease, Amyloid-β (Aβ) toxicity, Friedreich's ataxia, myotonic dystrophy, spinal muscular atrophy, fragile X syndrome, a spinocerebellar ataxia, Kennedy's disease, amyotrophic lateral sclerosis, Niemann Pick, Pitt Hopkins, spinal and bulbar muscular atrophy, infectious diseases, inflammatory diseases selected from allergy, asthma, autoimmune diseases, coeliac disease, glomerulonephritis, hepatitis, inflammatory bowel disease, reperfusion injury and transplant rejection, heart failure and cardiac hypertrophy, diabetes, polycystic kidney disease, and sickle cell disease (SCD) and β-thalassemia disease. The Central nervous system (CNS) cancer is selected from meningioma, neuroblastoma, glioblastoma, medullo blastoma, glioma, astrocytomas, oligodendrogliomas, ependymomas, gangliogliomas, neurilemmomas (Schwannomas), and craniopharyngiomas.

Aspect 7) combination products of the compounds of aspect 1 with one more therapeutic agent selected from the group consisting of chemotherapeutics agents, anti-inflammatory agents, steroids, immunosuppressants, therapeutic antibodies and adenosine antagonists, that can be used in combination with the compounds of the present application for treatment of HDAC associated diseases, disorders or conditions. The one or more additional pharmaceutical agents can be administered to a patient simultaneously or sequentially.

Example chemotherapeutics include proteosome inhibitors (e.g., bortezomib), chemotherapeutics agents for treatment of CNS cancer including temozolomide, carboplatin, carmustine (BCNU), cisplatin, cyclophosphamide, etoposide, irinotecan, lomustine (CCNU), methotrexate, procarbazine, vincristine, and other chemotherapeutics agents such as thalidomide, revlimid, and DNA-damaging agents such as melphalan, doxorubicin, cyclophosphamide, vincristine, etoposide, carmustine, and the like.

Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, valdecoxib, and the like.

Example steroids include corticosteroids such as cortisone, dexamethasone, hydrocortisone, methylprednisolone, prednisolone, prednisone, and the like.

Example immunosuppressants include azathioprine, chlorambucil, cyclophosphamide, cyclosporine, daclizumab, infliximab, methotrexate, tacrolimus, and the like.

Example of therapeutic antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20) and antibodies directed to c-MET.

Example of adenosine antagonist agents for use in combination therapy include but are not limited to CPI-444; PBF-509; and AZD4635 (HTL-1071).

In still another aspect (Aspect 8) the present invention relates to a combination product comprising compound of formula (I) or its pharmaceutically acceptable salts thereof and one or more immunotherapeutic agent useful in the treatment of cancer, more preferably colon, lung, breast, central nervous system cancer selected from meningioma, neuroblastoma, glioblastoma, medullo blastoma, glioma, astrocytomas, oligodendrogliomas, ependymomas, gangliogliomas, neurilemmomas(Schwannomas), and craniopharyngiomas, uterine cervical cancer, pancreatic adenocarcinoma, hepatocellular carcinoma, gastric cancer, tissue cancer and T-cell malignances such as leukemias and lymphomas, e.g., acute myeloid leukemia, acute lymphoblastic leukemia, cutaneous T-cell lymphoma, peripheral T-cell lymphoma, B-cell lymphoma and multiple myeloma.

In a preferred embodiment, a combination product comprises a compound of formula (I) or a pharmaceutically acceptable salt or co-crystal thereof, and one or more immunotherapeutic agent selected from the group consisting of antibodies anti-CTLA4, such as Ipilimumab and Tremelimumab, antibodies anti-PD1 such as MDX-1106 (nivolumab), MK3475 (pembrolizumab), CT-011 (pidilizumab) and AMP-224 and antibodies anti-PDL1 such as MPDL3280A (atezolizumab), MEDI4736 (durvalumab) and MDX-1105. The components of the combination product are in the same formulation or in separate formulations.

In other preferred embodiment, a combination product comprises a compound of formula (I) or a pharmaceutically acceptable salt or co-crystal thereof, and one or more chemotherapeutics agent selected from the group consisting of Carboplatin, Carmustine (BCNU), Cisplatin, Cyclophosphamide, Etoposide, Irinotecan, Lomustine (CCNU), Methotrexate, Procarbazine, Temozolomide, Vincristine.

Accordingly, the derivatives of the present invention and pharmaceutically acceptable salts and pharmaceutical compositions comprising such compounds and/or salts thereof, may be used in a method of treatment of pathological conditions or disease of human body which comprises administering to a subject in need of said treatment, an effective amount of the heteroaryl amide derivatives of the invention or a pharmaceutically acceptable salt thereof.

As it is said before, the heteroaryl amide derivatives of the invention are useful in the treatment or prevention of diseases known to be susceptible to amelioration by treatment with inhibitors of histone deacetylase class I, selected from HDAC1 and HDAC2. Such diseases comprise cancer such as colon, lung, breast, central nervous system (CNS) cancer selected from meningioma, neuroblastoma, glioblastoma, medullo blastoma, glioma, astrocytomas, oligodendrogliomas, ependymomas, gangliogliomas, neurilemmomas (Schwannomas), and craniopharyngiomas, uterine cervical cancer, pancreatic adenocarcinoma, hepatocellular carcinoma, gastric cancer, tissue cancer and T-cell malignancies such as leukemias and lymphomas, e.g., acute myeloid leukemia, acute lymphoblastic leukemia, cutaneous T-cell lymphoma, peripheral T-cell lymphoma, B-cell lymphoma and multiple myeloma; neurodegenerative diseases selected from Alzheimer's disease, post-traumatic stress disorder, drug addiction, Parkinson's disease, Huntington's disease, Amyloid-β (Aβ) toxicity, Friedreich's ataxia, myotonic dystrophy, spinal muscular atrophy, fragile X syndrome, a spinocerebellar ataxia, Kennedy's disease, amyotrophic lateral sclerosis, Niemann Pick, Pitt Hopkins, spinal and bulbar muscular atrophy; infectious diseases, inflammatory diseases selected from allergy, asthma, autoimmune diseases, coeliac disease, glomerulonephritis, hepatitis, inflammatory bowel disease, reperfusion injury and transplant rejection; heart failure and cardiac hypertrophy; diabetes, polycystic kidney disease and sickle cell disease (SCD) and β-thalassemia disease.

As used herein, the term halogen atom comprises chlorine, fluorine, bromine or iodine atoms, preferably fluorine, chlorine or bromine atoms. The term halo when used as a prefix has the same meaning.

As used herein, the term haloalkyl is used to designate $C_1$-$C_4$ alkyl substituted by one or more halogen atoms, preferably one, two or three halogen atoms. Preferably, the halogen atoms are selected from the group consisting of fluorine or chlorine atoms. In a preferred embodiment, the haloalkyl groups are $C_1$-$C_4$ alkyl substituted by one, two or three fluorine or chlorine atoms.

As used herein the term alkyl group is used to designate linear or branched hydrocarbon radicals ($C_nH_{2n+1}$) having 1 to 6 carbon atoms. Examples include methyl, ethyl, n-propyl, i-propyl, n-butyl, sec-butyl, tert-butyl, n-pentyl, 1-methyl-butyl, 2-methyl-butyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3dimethylbutyl, 2,2-dimethylbutyl, 2,3-dimethylbutyl, 2-methylpentyl and 3-methylpentyl radicals. In a preferred embodiment said alkyl groups have 1 to 3 carbon atoms ($C_1$-$C_3$ alkyl).

As used herein, the term cycloalkyl embraces hydrocarbon cyclic groups having 3 to 12 carbon atoms. Said cycloalkyl groups may have a single cyclic ring or multiple condensed rings. Such cycloalkyl groups include, by way of example, single ring structures such as cyclopropyl, cyclobutyl, cyclopentyl, cyclohexyl, and the like, or multiple ring structures such as adamantanyl, bicyclo[2.2.1]heptane, 1,3,3trimethylbicyclo[2.2.1]hept-2-yl, (2,3,3-trimethylbicyclo[2.2.1]hept-2-yl). In a preferred embodiment said cycloalkyl groups embraces hydrocarbon cyclic groups having 3 to 6 carbon atoms.

As used herein, the term $C_1$-$C_4$ alkoxy is used to designate radicals which contain a linear or branched $C_1$-$C_4$ alkyl group linked to an oxygen atom ($C_nH_{2n+1}$—O—). Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein the term cycloalkoxy is used to designate radicals containing a $C_3$-$C_6$ cycloalkyl groups linked to an oxygen atom.

As used herein, the terms five or six-membered heteroaryl ring and $C_5$-$C_6$ heteroaryl ring are used indistinctively to designate heteroaromatic rings containing carbon, hydrogen and one or more heteroatom selected from N, O and S as part of the ring. The preferred groups are optionally substituted pyridyl, pyrimidinyl, thienyl. When a heteroaryl radical carries 2 or more substituents, the substituents may be the same or different.

As used herein, the term $C_5$-$C_6$ heterocyclic ring and five or six membered saturated heterocycle are used indistinctively to designate saturated heterocyclic ring containing carbon, hydrogen and one or more heteroatoms selected from N and O as part of the ring. Said groups may optionally be substituted by one or more substituents. The preferred radicals are optionally substituted piperidinyl, piperazinyl and morpholinyl. When heterocyclic radical carries 2 or more substituents, the substituents may be the same or different.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different As used herein, the term pharmaceutically acceptable salt is used to designate salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

Other preferred salts according to the invention are quaternary ammonium compounds wherein an equivalent of an anion ($X^{-n}$) is associated with the positive charge of the N atom. $X^{-n}$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. $X^{-n}$ is preferably an anion selected from chloride, bromide, iodide, sulphate, nitrate, acetate, maleate, oxalate, succinate or trifluoroacetate. More preferably, X— is chloride, bromide, trifluoroacetate or methanesulphonate.

As used herein, the term "inhibitor" refers to a molecule such as a compound, a drug, enzyme, or a hormone that blocks or otherwise interferes with a particular biologic activity. The term "inhibitor" is synonymous with the term antagonist.

The term "HDAC1/2 selective" means that the compound binds to HDAC1 and HDAC2 to a substantially greater extent, such as 5×, 10×, 15×, 20× greater or more, than to any other type of HDAC enzyme, such as HDAC3 or HDAC6. That is, the compound is selective for HDAC1 and/or HDAC2 over any other type of HDAC enzyme.

According to one embodiment of the present invention, $X^1$ is a —CH group. In a more preferred embodiment, $X^1$ and $X^2$ are —CH groups.

According to one embodiment of the present invention $R^1$ represents a phenyl group optionally substituted by one or more substituents selected from the group consisting of halogen atoms, $C_1$-$C_4$ haloalkyl and $C_1$-$C_4$ alkoxy. In a more preferred embodiment $R^1$ represents a phenyl group optionally substituted by one or more substituents selected from halogen atoms.

In another embodiment of the present invention $R^1$ represents a five or a six-membered heteroaryl ring optionally substituted by one or more substituents selected from the group consisting of cyano group, halogen atom and $C_1$-$C_4$ haloalkyl. In a more preferred embodiment $R^1$ represents pyridyl or thienyl ring.

According to one embodiment of the present invention $R^2$ represent —N($R^3$)($R^4$) group, wherein $R^3$ and $R^4$ form together with the nitrogen atom to which they are bound a 5 or 6 membered saturated heterocycle comprising optionally a heteroatom selected from N and O as part of the cycle, which heterocycle is optionally substituted by a $C_1$-$C_3$ alkyl group or an —N($R^5$)($R^6$) group, wherein $R^5$ and $R^6$ form together with the nitrogen atom to which they are bound a five or six-membered saturated cycle comprising optionally an additional heteroatom selected from N and O as part of the cycle, which cycle is optionally substituted by a $C_1$-$C_3$ alkyl group. In a more preferred embodiment $R^2$ represent piperazinyl, piperidinyl or morpholinyl ring optionally substituted by a $C_1$-$C_3$ alkyl group or an —N($R^5$)($R^6$) group.

According to one embodiment of the present invention $R^2$ represent —N($R^3$)($R^4$) group, wherein $R^3$ and $R^4$ represent independently a group selected from hydrogen atom, $C_3$-$C_6$ cycloalkyl group and $C_1$-$C_3$ alkyl linear or branched, which is optionally substituted by a 5 or 6-membered heterocycle comprising one or two N atom as part of the cycle, which cycle is optionally substituted by a $C_1$-$C_3$ alkyl group. In a more preferred embodiment $R^2$ represent —N($R^3$)($R^4$) group, wherein $R^3$ represents $C_1$-$C_3$ alkyl linear substituted by a 5 or 6-membered saturated heterocycle comprising one or two N atom, which heterocycle is optionally substituted by a $C_1$-$C_3$ alkyl group; and $R^4$ is a hydrogen atom.

According to one embodiment of the present invention $R^2$ represent a phenyl ring optionally substituted by one or more substituents selected from halogen atoms and cyano group. In a preferred embodiment, the phenyl ring is substituted by one halogen atoms or by one cyano group.

According to another embodiment of the present invention $R^2$ represent a $C_3$-$C_6$ cycloalkyl. In a more preferred embodiment $R^2$ represent cyclopropyl or a cyclopentyl ring.

According to another embodiment of the present invention $R^2$ represent a $C_5$-$C_6$ heteroaryl optionally substituted by one or more substituents selected from halogen atoms and cyano group. In a preferred embodiment $C_5$-$C_6$ heteroaryl is substituted by one halogen atoms or by one cyano group. In a more preferred embodiment $R^2$ represent pyridyl or pyrimidinyl ring optionally substituted by one or more substituents selected from halogen atoms and cyano group, preferably substituted by one halogen atoms or by one cyano group.

In a further preferred embodiment of the present invention in the compounds of formula (I), $X^1$ and $X^2$ represents —CH groups, $R^1$ represents a phenyl group optionally substituted by one or more halogen atoms, and $R^2$ represents —N($R^3$)($R^4$) group wherein $R^3$ and $R^4$ form together with the nitrogen atom to which they are bound a 6 membered saturated heterocycle comprising optionally a heteroatom selected from N and O, which is optionally substituted by a $C_1$-$C_3$ alkyl group or an —N($R^5$)($R^6$) group, wherein $R^5$ and $R^6$ form together with the nitrogen atom to which they are bound a five or six-membered saturated cycle comprising optionally an additional heteroatom selected from N and O, which is optionally substituted by a $C_1$-$C_3$ alkyl group. In a more preferred embodiment $R^2$ represents a piperazinyl ring optionally substituted by a $C_1$-$C_3$ alkyl group.

Particular individual compounds of the present invention include:

N-(3-amino-6-phenylpyridin-2-yl)-6-(4-methylpiperazin-1-yl)nicotinamide

N-(3-amino-6-phenylpyridin-2-yl)nicotinamide

N-(3-amino-6-(4-fluorophenyl)pyridin-2-yl)nicotinamide

N-(3-amino-6-phenylpyridin-2-yl)-6-morpholinonicotinamide

N-(3-amino-6-(4-fluorophenyl)pyridin-2-yl)-6-morpholinonicotinamide

N-(3-amino-6-(4-fluorophenyl)pyridin-2-yl)-6-(4-methylpiperazin-1-yl)nicotinamide N-(3-amino-6-(4-methoxyphenyl)pyridin-2-yl)-6-(4-methylpiperazin-1-yl)nicotinamide N-(5-amino-[2,4'-bipyridin]-6-yl)-6-(4-methylpiperazin-1-yl)nicotinamide N-(3-amino-6-(3,4-difluorophenyl)pyridin-2-yl)-6-(4-methylpiperazin-1-yl)nicotinamide N-(3-amino-6-phenylpyridin-2-yl)-2-(4-methylpiperazin-1-yl)pyrimidine-5-carboxamide N-(3-amino-6-phenylpyridin-2-yl)pyrimidine-5-carboxamide N-(3-amino-6-(4-fluorophenyl)pyridin-2-yl)pyrimidine-5-carboxamide N-(3-amino-6-(4-fluorophenyl)pyridin-2-yl)-6-(4-methylpiperazin-1-yl)nicotinamide N-(3-amino-6-(4-fluorophenyl)pyridin-2-yl)-2-morpholinopyrimidine-5-carboxamide N-(3-amino-6-(4-fluorophenyl)pyridin-2-yl)-2-(4-methylpiperazin-1-yl)pyrimidine-5-carboxamide N-(3-amino-6-phenylpyridin-2-yl)-2-(cyclopropylamino)pyrimidine-5-carboxamide N-(3-amino-6-(4-fluorophenyl)pyridin-2-yl)-2-(cyclopropylamiflo)pyrimidine-5-carboxamide
N-(3-amino-6-(4-fluorophenyl)pyridin-2-yl)-6-phenylnicotinamide
N-(3-amino-6-(4-fluorophenyl)pyridin-2-yl)-6-(4-fluorophenyl)nicotinamide
N-(3-amino-6-(4-fluorophenyl)pyridin-2-yl)-[2,4'-bipyridine]-5-carboxamide
N-(3-amino-6-(4-fluorophenyl)pyridin-2-yl)-[2,3'-bipyridine]-5-carboxamide
N-(3-amino-6-(4-fluorophenyl)pyridin-2-yl)-6-(3-cyanophenyl)nicotinamide
N-(3-amino-6-(4-fluorophenyl)pyridin-2-yl)-6-cyclopropylnicotinamide
N-(3-amino-6-(4-fluorophenyl)pyridin-2-yl)-6-cyclopentylnicotinamide
N-(3-amino-6-(4-fluorophenyl)pyridin-2-yl)-6-(piperazin-1-yl)nicotinamide
N-(5-amino-2-(4-fluorophenyl)pyrimidin-4-yl)-6-(piperazin-1-yl)nicotinamide
N-(3-amino-6-(4-fluorophenyl)pyridin-2-yl)-6-(4-aminopiperidin-1-yl)nicotinamide
N-(5-amino-2-(4-fluorophenyl)pyrimidin-4-yl)-6-(4-aminopiperidin-1-yl)nicotinamide
N-(3-amino-6-(thiophen-2-yl)pyridin-2-yl)-6-(4-methylpiperazin-1-yl)nicotinamide
N-(3-amino-6-(4-fluorophenyl)pyridin-2-yl)-6-((2-(4-methylpiperazin-1-yl)ethyl)amino)nicotinamide
N-(3-amino-6-(4-fluorophenyl)pyridin-2-yl)-6-((2-(pyridin-3-yl)ethyl)amino)nicotinamide The synthesis of compound of formula (I) is outlined in the following schemes.

In Scheme 1 the synthesis of intermediate compound of formula (IV) is described.

Scheme 1

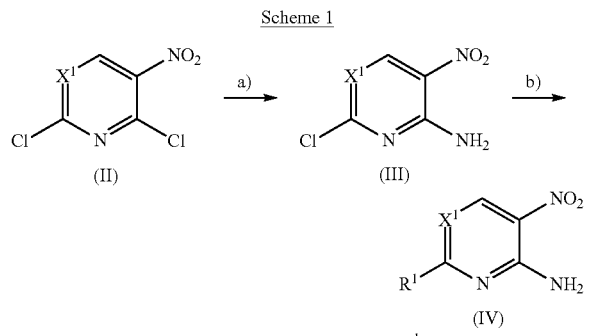

Reagents and conditions: a) NH$_3$, EtOH, 0° C.-RT, 3-6 h; b) R$^1$—B(OH)$_2$, Pd$_2$(dba)$_3$, SPhos, K$_3$PO$_4$, Toluene/H$_2$O, refluxed overnight.

The commercially available reagents of formula (II) are reacted with ammonia in ethanol at 0° C. to afford the derivatives of formula (III). Suzuki-type coupling with boronic acid or boronate derivatives using a palladium catalyst such as Tris(dibenzylideneacetone)dipalladium(0) in the presence of SPhos (dicyclohexyl(2',6'-dimethoxy-[1,1'-biphenyl]-2-yl)phosphine) and an aqueous solution of a base such as potassium phosphate tribasic monohydrate at 110° C. during 12 h provide the compounds of formula (IV), according to Scheme 1.

In Scheme 2 the synthesis of intermediate compound of formula (VI) is described.

Scheme 2

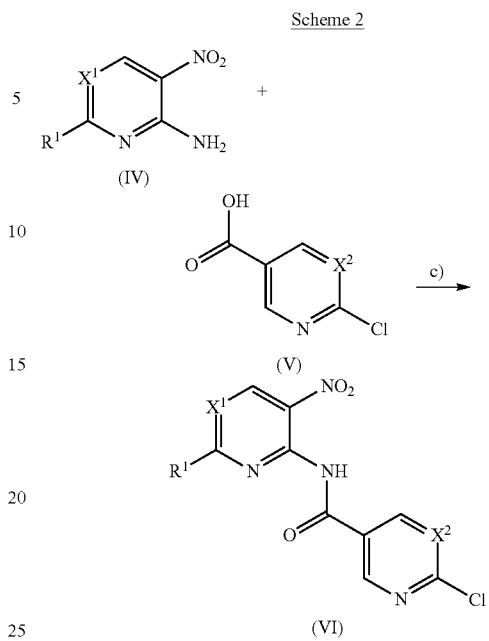

Reagents and conditions: c) ethyl chloro formate, TEA, NaHMDS, THF, -35° C.-room temp.

For the preparation of the amides of formula (VI) the carboxylic acid of formula (V) is activated in form of a mixed anhydride. This anhydride is generated reacting the corresponding acid with ethyl chloro formate in the presence of triethyl amine. The synthesis of the amides of formula (VI) is carried out by the reaction of the heteroaryl amine of formula (IV) with the correspondent mixed carboxylic acid anhydride in the presence of a base, for example sodium bis(trimethylsilyl)amide (NaHMDS) at temperatures between −35° C. to room temperature.

In Scheme 3 the synthesis of compounds of formula (I) according to the present invention wherein R2 is a phenyl or heteroaryl ring is described.

Scheme 3

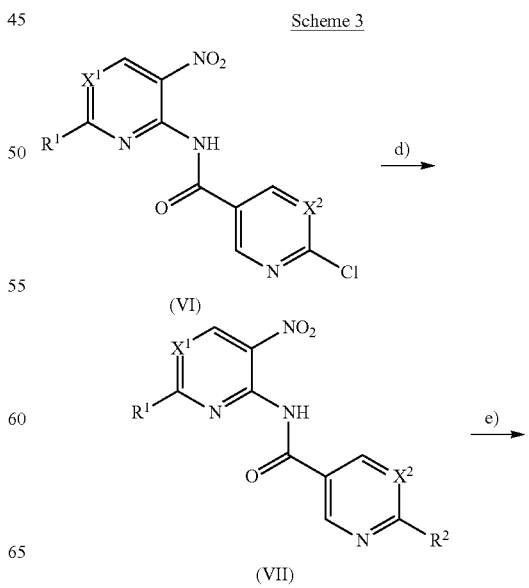

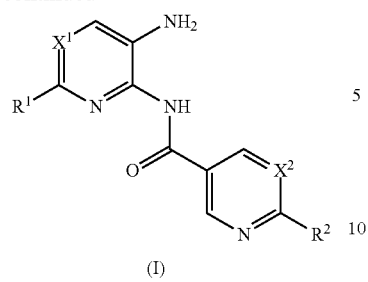

(I)

Reagents and conditions: d) R²—B(OH)₂, Pd₂(dba)₃, SPhos, K₃PO₄, Toluene/H₂O, refluxed overnight/primary or secondary amine, DIPEA, DMSO, 110° C.; e) H₂, (Pd/C).

The compounds of general formula (I) are prepared in two steps from intermediates of formula (VI). When R² represents an optionally substituted cycloalkyl, phenyl or heteroaryl groups, according to the present invention, the group R² is introduced by a Suzuki-type coupling with the corresponding boronic acids or boronate derivatives, using the standard procedures for palladium catalyzed reaction to provide compounds of formula (VII).

In Scheme 4 the synthesis of compounds of formula (I) according to the present invention wherein R² is —N(R³)(R⁴) is described.

Scheme 4

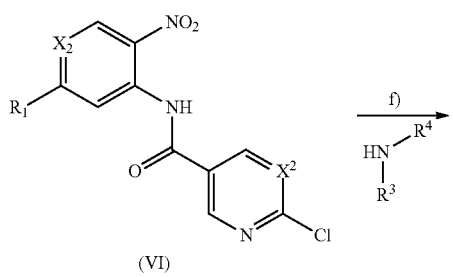

(VI)

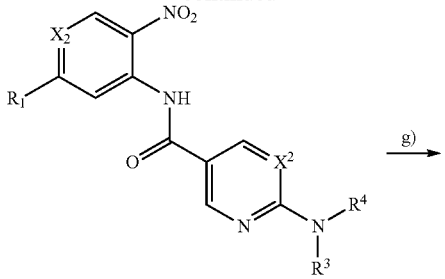

(VIIa)

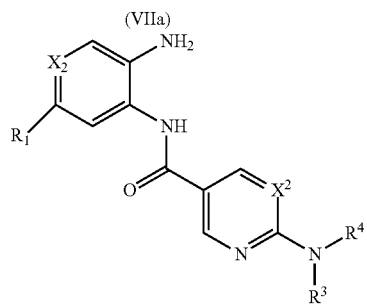

(Ia)

Reagents and conditions: f) R₂—B(OH)₂, Pd₂(dba)3, SPhos, K₃PO₄, Toluene/H₂O, refluxed overnight/——N(R³)(R⁴), DIPEA, DMSO, 110° C.;
g) H₂, (Pd/C).

In the cases where R² represents an —NR³R⁴ group, according to the definition of the present invention, the reaction of the intermediate (VI) with primary or secondary amines in the presence of N,N-diisopropylethylamine (DIPEA) in DMSO at 110° C. leads to the compounds of formula (VIIa).

Subsequent reduction of the nitro group of compounds of formula (VIIa) take place with hydrogen gas in the presence of palladium catalyst (Pd/C) as described in Scheme 3 providing compounds of formula (I), which are the subject of the present invention.

Alternatively, the compounds of formula (I) of the present invention can be also prepared using the same reactions as described above but employing the sequence represented in Scheme 5.

Scheme 5

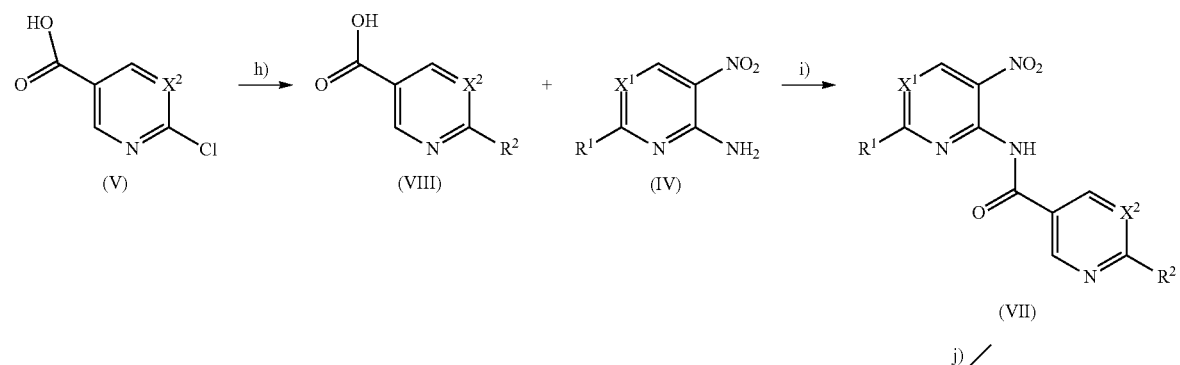

-continued

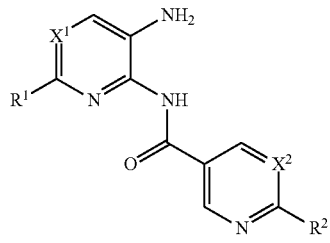

(I)

Reagents and conditions: h) $R^2$—B(OH)$_2$, Pd$_2$(dba)$_3$, SPhos, K$_3$PO$_4$, Toluene/H$_2$O, refluxed overnight/primary or secondary amine, DIPEA, DMSO, 110° C.; i) ethyl chloro formate, TEA, NaHMDS, THF, -35° C.-room temp; j) H$_2$, (Pd/C).

Pharmacological Activity
Histone Deacetylase Assay

The inhibitory activities of compounds of present invention were determined using biochemical HDAC assays (Reaction Biology Corp. biochemical assay services). Compound with indicated doses was tested in the biochemical assays of HDAC 1, HDAC2, HDAC3, HDAC4, HDAC5, HDAC6, HDAC7, HDAC 8, HDAC9, HDAC10, and HDAC11 enzyme.

Compounds were tested in singlicate 10-dose IC$_{50}$ mode with 3-fold serial dilution starting at 10 μM against 11 HDACs. HDAC reference compounds Trichostatin A (TSA) and TMP269 were tested in a 10-dose IC$_{50}$ with 3-fold serial dilution starting at 10 μM.

Substrate for HDAC1,2,3,6,10: Fluorogenic peptide from p53 residues 379-382 (RHKK(Ac)AMC). Substrate for HDAC4,5,7,9, and 11: Fluorogenic HDAC Class2a Substrate (Trifluoroacetyl Lysine). Substrate for HDAC 8: Fluorogenic peptide from p53 residues 379-382 (RHK(Ac)K(Ac)AMC).

General Reaction Procedure: (Standard IC50 determination)
a. 2× enzyme was added to wells of reaction plate except to No Enzyme (No En) control wells. Add buffer in No En wells.
b. Compounds to be tested in 100% DMSO were added to the enzyme mixture by Acoustic technology (Echo550; nanoliter range). The mixture was spinned down and preincubated.
c. 2× Substrate Mixture (Fluorogenic HDAC Substrate and co-factor (500 μM of Nicotinamide adenine dinucleotide (NAD<+>) in all Sirt assay) were added to all reaction wells to initiate the reaction. The plates were spinned and shaken.
d. The plates were incubated for 1-2 hr. at 30° C. with seal.
e. Developer with Trichostatin A (or TMP269 or NAD<+>) was added to stop the reaction and to generate fluorescent color.
f. Fluorescence was read (excitatory, 360; emission, 460) using the EnVision Multilabel Plate Reader (Perkin Elmer)
g. Endpoint reading was taken for analysis after the development reaches plateau.

Data Analysis: The percentages of enzyme activity (relative to DMSO controls) and IC$_{50}$ values were calculated using the GraphPad Prism 4 program based on a sigmoidal dose-response equation. The blank (DMSO) value was entered as 1.00E-12 of concentration for curve fitting.

Results

Results for selected compounds of the invention in the HDAC activity inhibition assay are shown in Table 1 (IC$_{50}$ Ranges: A<0,2 μM; 0,2 μM<B<1 μM; 1 μM<=C<50 μM m, D>=50 μM).

TABLE 1

| Example No. | IC$_{50}$ HDAC 1 (μM) | IC$_{50}$ HDAC2 (μM) | IC$_{50}$ HDAC3 (μM) | IC$_{50}$ HDAC8 (μM) | IC$_{50}$ HDAC6 (μM) | IC$_{50}$ HDAC10 (μM) |
|---|---|---|---|---|---|---|
| 1 |  | A |  |  |  |  |
| 2 |  | A |  |  |  |  |
| 3 |  | A |  |  |  |  |
| 4 |  | A |  |  |  |  |
| 5 | A | A | D | D |  | C |
| 6 | A | A | D | D | D | C |
| 7 |  | B |  |  |  |  |
| 8 |  | B |  |  |  |  |
| 9 |  | B |  |  |  |  |
| 10 |  | A |  |  |  |  |
| 13 |  | A |  |  |  |  |
| 14 |  | A |  |  |  |  |
| 15 |  | A |  |  |  |  |
| 16 |  | A |  |  |  |  |
| 17 | C | A | D |  |  | D |
| 21 |  | B |  |  |  |  |
| 22 |  | B |  |  |  |  |
| 24 |  | B |  |  |  |  |
| 25 | B | A | D | D | C | C |
| 27 | A | A | D |  | C | C |
| 29 | A | A | C |  | C | C |
| 30 |  | A |  |  |  |  |

* Empty cells: indicate no inhibition or compound activity that could not be fit to an IC$_{50}$ curve As can be seen from the results described in Table 1, the compounds of the present invention are potent inhibitor of the histone deacetylases 1 and/or 2 (HDAC1 and/or HDAC2).

In some embodiments, as can be seen from the results described in Table 1, the compounds of the present invention are potent and selective inhibitors of HDAC1 and HDAC2 over other histone deacetylase subtypes.

Accordingly, the derivatives of the invention and pharmaceutically acceptable salts thereof, and pharmaceutical compositions comprising such compounds and/or salts thereof, may be used in a method of treatment of disorders of the human body which comprises administering to a subject requiring such treatment an effective amount of the compound of formula (I) or a pharmaceutically acceptable salt thereof.

Compounds of the invention are useful in the treatment or prevention of diseases known to be susceptible to improvement by inhibition of histone deacetylase class I, particularly histone deacetylases 1 and 2 (HDAC1, HDAC2). Such diseases are selected from cancer; neurodegenerative diseases; infectious diseases; inflammatory diseases; heart failure and cardiac hypertrophy; diabetes; polycystic kidney disease, and sickle cell disease (SCD) and β-thalassemia disease.

One therapeutic use of the compounds of the present invention is to treat proliferative diseases or disorders such as cancer. Cancer include colon, lung, breast, central nervous system (CNS) cancer, uterine cervical cancer, pancreatic adenocarcinoma, hepatocellular carcinoma, gastric cancer, tissue cancer and T-cell malignances selected from acute myeloid leukemia, acute lymphoblastic leukemia, cutaneous T-cell lymphoma, peripheral T-cell lymphoma, B-cell lymphoma and multiple myeloma. Central nervous system (CNS) cancer include meningioma, neuroblastoma, glioblastoma, medullo blastoma, glioma, astrocytomas, oligodendrogliomas, ependymomas, gangliogliomas, neurilemmomas(Schwannomas), and craniopharyngiomas.

Another therapeutic use of the compounds of the present invention is also to treat neurodegenerative diseases selected from Alzheimer's disease, post-traumatic stress disorder or drug addiction, Parkinson's disease, Huntington's disease, Amyloid-$\beta$ (A$\beta$) toxicity, Friedreich's ataxia, myotonic dystrophy, spinal muscular atrophy, fragile X syndrome, a spinocerebellar ataxia, Kennedy's disease, amyotrophic lateral sclerosis, Niemann Pick, Pitt Hopkins, spinal and bulbar muscular atrophy.

Another therapeutic use of the compounds of the present invention is also to treat viral infections diseases or disorders. such as HIV.

Another therapeutic use of the compounds of the present invention is also to treat inflammatory diseases selected from allergy, asthma, autoimmune diseases, coeliac disease, glomerulonephritis, hepatitis, inflammatory bowel disease, reperfusion injury and transplant rejection.

The present invention also provides pharmaceutical compositions which comprise, as an active ingredient, at least a heteroaryl amide derivatives of formula (I) or a pharmaceutically acceptable salt thereof in association with other therapeutics agents and a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably, the compositions are made up in a form suitable for oral, topical, nasal, rectal, percutaneous or injectable administration.

The pharmaceutically acceptable excipients, which are admixed with the active compound or salts of such compound, to form the compositions of this invention, are well known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in any way. The synthesis of the compounds of the invention is illustrated by the following examples including the preparation of the intermediates, which do not limit the scope of the invention in any way.

Abbreviations

In the present application are used the following abbreviations, with the corresponding definitions:
RT: Room temperature
Pd2(dba)3: Tris(dibenzylideneacetone)dipalladium
SPhos: dicyclohexyl(2',6'-dimethoxy-[1,1'-biphenyl]-2-yl)phosphine
TEA: Triethylamine
NaHMDS: Sodium bis(trimethylsilyl)amide
THF: Tetrahydrofuran
DMSO: Dimethyl sulfoxide

EXAMPLES

General.

Reagents, solvents and starting products were acquired from commercial sources. The term "concentration" refers to the vacuum evaporation using a Büichi rotavapor. When indicated, the reaction products were purified by "flash" chromatography on silica gel (40-63 µm) with the indicated solvent system. The spectroscopic data were measured in a Varian Mercury 400 spectrometer. The melting points were measured in a Büichi 535 instrument. The HPLC-MS were performed on a Gilson instrument equipped with a Gilson 321 piston pump, a Gilson 864 vacuum degasser, a Gilson 189 injection module, a 1/1000 Gilson splitter, a Gilson 307 pump, a Gilson 170 detector, and a Thermoquest Fennigan aQa detector.

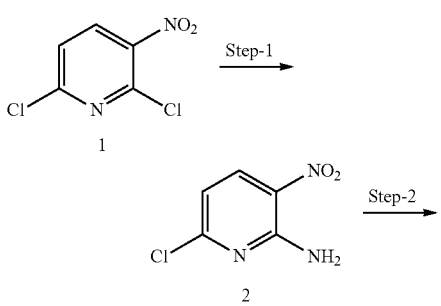

Scheme 6: Synthesis of Example 1

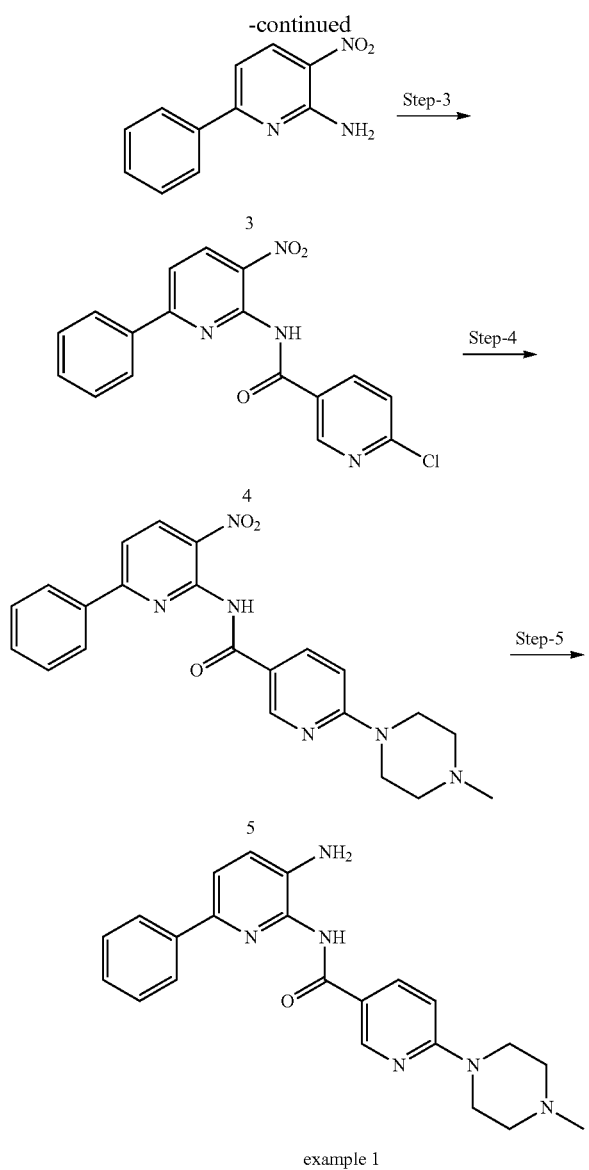

example 1

Step-1: Synthesis of 6-chloro-3-nitropyridin-2-amine (Intermediate 2)

A solution of compound 1 (5 g. 0.026 mol) in ethanol (50 ml) at 0° C. was purged with ammonia gas for 3 h, then allowed to stir overnight at room temperature. The reaction mixture was diluted with water, and the precipitate that formed was filtered and washed with water, followed by hexane and dried to obtain Intermediate 2 (3.65 g, 81.2% yield).

Step-2: Synthesis of 3-nitro-6-phenylpyridin-2-amine (Intermediate 3)

Intermediate 2 (8.62 g, 0.05 mol), phenylboronic acid (5.05 g), dicyclohexyl(2',6'-dimethoxy-[1,1'-biphenyl]-2-yl)phosphine (0.567 g), potassium phosphate tribasic monohydrate (23.85 g), 30 mL toluene and 3 mL water were added to a 3-neck 100 mL round bottom flask. Nitrogen was bubbled directly into the mixture for 20 minutes. $Pd_2(dba)_3$ (0.316 g) was added and the mixture refluxed overnight under nitrogen. The reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography eluting with 20% ethyl acetate/hexanes initially and ethyl acetate was added to flush off the product. The product was washed with hexane to get intermediate 3 (8.02 g, 75% yield).

Step-4: Synthesis of 6-chloro-N-(3-nitro-6-phenylpyridin-2-yl)nicotinamide (Intermediate 4)

A solution of 6-chloro-3-nicotonic acid (1 g) in THF (10 ml), TEA (1.5 ml) and ethyl chloro formate (1.45 ml) was added and allowed to stir 1 h at room temperature. The reaction mixture was diluted with water, and the precipitate that formed was filtered and dried to obtain anhydride. A solution of intermediate 3 (1 g) in THF (50 ml), NaHMDS (10 ml) was added slowly at −35'C and allowed to stir 1 h at same temperature. To this solution, anhydride (1.2 g) in THF (5 ml) was added immediately and allowed the reaction mixture warm to room temperature. After completion, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 4 (0.96 g, 78% yield).

Step-5: Synthesis of 6-(4-methylpiperazin-1-yl)-N-(3-nitro-6-phenylpyridin-2-yl)nicotinamide (Intermediate 5)

To a solution N-methyl-piperazine (226 mg) in DMSO (10 v) was added DIPEA (437 mg) and intermediate 4 (400 mg) was heated in seal tube at 110° C. for overnight. After completion of the reaction monitored by TLC, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 5 as pale yellow solid (310 mg, 67% yield).

Step-6: Synthesis of N-(3-amino-6-phenylpyridin-2-yl)-6-(4-methylpiperazin-1-yl)nicotinamide. Example 1

To a solution intermediate 5 (310 mg) in ethanol (20 ml) and ethyl acetate (35 ml) was added Pd/C (10%) (46 mg, 15% (w/w)) and allowed reaction to stir for overnight under hydrogen gas. After completion of the reaction monitored by TLC, the reaction mixture was filtered through celite and evaporated to a residue. The residue was purified by Prep. HPLC to obtain example 1 as off-white solid (20 mg, 10% yield).

$^1$H-NMR (400 MHz, DMSO-$d_6$): δ=10.25 (br, s, 1H), 8.80 (d, J=4.4 Hz, 1H), 8.15 (d, J=11.6 Hz, 1H), 7.955 (d, J=7.2 Hz, 2H), 7.68 (d, J=8.0 Hz, 1H), 7.42 (t, J=7.6 Hz, 2H), 7.31 (m, 2H), 6.92 (d, J=9.2 Hz, 1H), 5.14 (br, s, 2H), 3.65 (t, J=4.8 Hz, 4H), 2.40 (t, J=4.8 Hz, 4H), 2.22 (s, 3H).

HPLC-MS: Rt 11.120 m/z 389.6 (MH$^+$).

The following examples were synthesized using the procedure described scheme 6 starting from the corresponding pyridin-2-amine and nicotinic acid derivatives.

Example 2: N-(3-amino-6-phenylpyridin-2-yl)nicotinamide $^1$H-NMR (400 MHz, DMSO-$d_6$): δ=10.60 (s, 1H), 9.18 (s, 1H), 8.77 (dd, J=6.0, 1.2 Hz, 1H), 8.37 (d, J=8.0 Hz, 1H), 7.94 (d, J=7.6 Hz, 2H), 7.71 (d, J=8.4 Hz, 1H), 7.58 (m, 1H), 7.42 (t, J=7.6 Hz, H), 7.31 (m, 2H), 5.29 (br s, 2H).
HPLC-MS: Rt 9.891 m/z 291.0 (MH$^+$).

Example 3: N-(3-amino-6-(4-fluorophenyl)pyridin-2-yl)nicotinamide $^1$H-NMR (400 MHz, DMSO-$d_6$) δ=10.59 (s, 1H), 9.17 (d, J=2.0 Hz, 1H), 8.77 (dd, J=6.8, 1.6 Hz, 1H), 8.37 (m, 1H), 7.98 (m, 2H), 7.69 (d, J=8.4 Hz, 1H), 7.58 (m, 1H), 7.26 (m, 3H), 5.29 (br, s, 2H).
HPLC-MS: Rt 10.590 m/z 309.0 (MH$^+$).

Example 4: N-(3-amino-6-phenylpyridin-2-yl)-6-morpholinonicotinamide $^1$H-NMR (400 MHz, DMSO-$d_6$) δ=10.27 (br, s, 1H), 8.28 (d, J=2.0 Hz, 1H), 8.19 (dd, J=11.0, 2.0 Hz, 1H), 7.96 (d, J=7.6 Hz, 2H), 7.68 (d, J=8.4 Hz, 1H), 7.42 (t, J=7.6 Hz, 2H), 7.31 (m, 2H), 6.93 (d, J=9.2 Hz, 1H), 5.15 (br, s, 2H), 3.72 (m, 4H), 3.60 (m, 4H).
HPLC-MS: Rt 9.828 m/z 376.3 (MH+).

Example 5: N-(3-amino-6-(4-fluorophenyl)pyridin-2-yl)-6-morpholinonicotinamide $^1$H-NMR (400 MHz, DMSO-$d_6$) δ=10.27 (br, s, 1H), 8.81 (d, J=2.4 Hz, 1H), 8.18 (dd, J=11.6, 2.4 Hz, 1H), 8.00 (m, 2H), 7.67 (d, J=8.0 Hz, 1H), 7.26 (m, 3H), 6.93 (d, J=8.8 Hz, 1H), 5.15 (br, s, 2H), 3.72 (m, 4H), 3.61 (m, 4H).
HPLC-MS: Rt 10.855 m/z 394.4 (MH+).

Example 6: N-(3-amino-6-(4-fluorophenyl)pyridin-2-yl)-6-(4-methylpiperazin-1-yl)nicotinamide $^1$H-NMR (400 MHz, DMSO-$d_6$) δ=10.24 (s, 1H), 8.79 (br, s, 1H), 8.15 (dd, J=11.6, 2.4 Hz, 1H), 8.00 (m, 2H), 7.69 (d, J=8.4 Hz, 1H), 7.26 (m, 3H), 6.92 (d, J=9.2 Hz, 1H), 5.14 (br, s, 2H), 3.65 (br, s, 4H), 2.55 (br, s, 4H), 2.22 (s, 3H).
HPLC-MS: Rt 11.906 m/z 407.4 (MH$^+$).

Example 7: N-(3-amino-6-(4-methoxyphenyl)pyridin-2-yl)-6-(4-methylpiperazin-1-yl)nicotinamide $^1$H-NMR (400 MHz, DMSO-$d_6$) δ=10.21 (s, 1H), 8.79 (d, J=2.8 Hz, 1H), 8.15 (dd, J=11.6, 2.4 Hz, 1H), 7.89 (d, J=8.8 Hz, 2H), 7.59 (d, J=8.0 Hz, 1H), 7.25 (d, J=8.4 Hz, 1H), 6.97 (m, 3H), 5.01 (br, s, 2H), 3.78 (s, 3H), 3.65 (t, J=4.8 Hz, 4H), 2.41 (t, J=4.8 Hz, 4H), 2.22 (s, 3H).
HPLC-MS: Rt 8.759 m/z 419.2 (MH$^+$).

Example 8: N-(5-amino-[2,4'-bipyridin]-6-yl)-6-(4-methylpiperazin-1-yl)nicotinamide $^1$H-NMR (400 MHz, DMSO-$d_6$) δ=10.22 (s, 1H), 8.79 (d, J=2.4 Hz, 1H), 8.57 (dd, J=6.4, 2.0 Hz, 2H), 8.14 (dd, J=11.6, 2.4 Hz, 1H), 7.90 (dd, J=6.4, 2.0 Hz, 2H), 7.84 (d, J=8.4 Hz, 1H), 7.27 (d, J=8.4 Hz, 1H), 6.92 (d, J=9.2 Hz, 1H), 5.43 (br, s, 2H), 3.65 (m, 4H), 2.41 (m, 4H), 2.22 (s, 3H).
HPLC-MS: Rt 3.743 m/z 390.2 (MH$^+$).

Example 9: N-(3-amino-6-(3,4-difluorophenyl)pyridin-2-yl)-6-(4-methylpiperazin-1-yl)nicotinamide $^1$H-NMR (400 MHz, DMSO-$d_6$) δ=10.09 (s, 1H), 8.75 (br, s, 1H), 8.10 (d, J=8.0 Hz, 1H), 7.90 (m, 1H), 7.75 (br, s, 1H), 7.66 (d, J=7.6 Hz, 1H), 7.41 (m, 1H), 7.23 (d, J=7.2 Hz, 1H), 6.87 (d, J=8.8 Hz, 1H), 5.15 (br, s, 2H), 3.61 (br, s, 4H), 2.38 (br, s, 4H), 2.2 (s, 3H).
HPLC-MS: Rt 10.548 m/z 425.2 (MH$^+$).

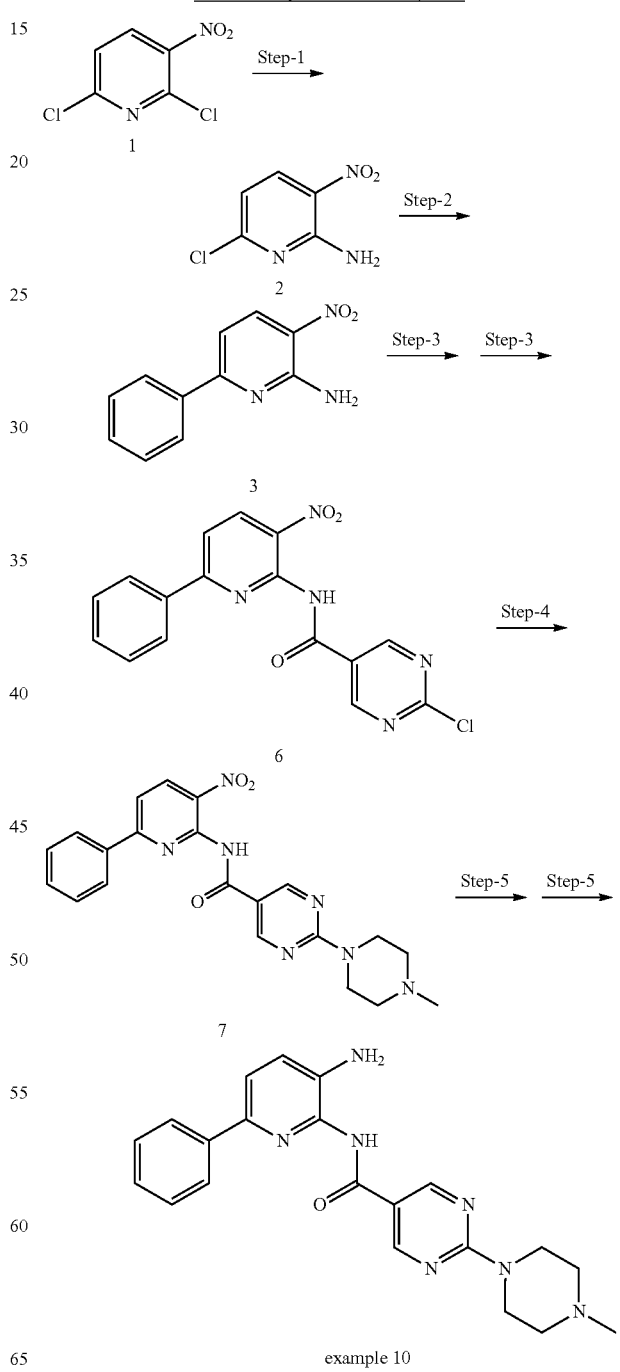

Scheme 7: Synthesis of Example 10

Step-3: Synthesis of 2-chloro-N-(3-nitro-6-phenylpyridin-2-yl)pyrimidine-5-carboxamide (Intermediate 6)

A solution of 2-chloropyrimidine-5-carboxylic acid (1 g) in THF (50 ml), TEA (2.73 g) and Ethyl chloro formate (1.7 g) was added and allowed to stir 1 h at room temperature. The reaction mixture was diluted with water (50 ml), and the precipitate that formed was filtered and dried to obtain anhydride. A solution of intermediate 3 (1 g) in THF (50 ml), NaHMDS (12.7 ml) was added slowly at −35° C. and allowed to stir 1 h at same temperature. To this solution, anhydride in THF (5 ml) was added immediately and allowed the reaction mixture warm to room temperature. After completion, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 6 (200 mg, 14% yield)

Step-7: Synthesis of 2-(4-methylpiperazin-1-yl)-N-(3-nitro-6-phenylpyridin-2-yl)pyrimidine-5-carboxamide (Intermediate 7)

To a solution, N-methyl-piperazine (141 mg) in DMF (4 ml) was added DIPEA (272 mg) and intermediate 4 (250 mg) was heated in seal tube at 80° C. for overnight. After completion of the reaction monitored by TLC, the reaction mixture was diluted with ethyl acetate/water. The layers were separated and the aqueous layer was extracted with ethyl acetate. The organic layer was dried over magnesium sulfate, filtered and evaporated to a residue. Crude was triturated with n-pentane to get intermediate 7 as pale brown solid (200 mg, 69% yield).

Step-8: Synthesis of N-(3-amino-6-phenylpyridin-2-yl)-2-(4-methylpiperazin-1-yl)pyrimidine-5-carboxamide. Example 10

To a solution intermediate 7 (200 mg) in ethanol (10 ml) and ethyl acetate (25 ml) was added Pd/C (10%) (30 mg, 15% (w/w)) and allowed reaction to stir for overnight under hydrogen gas. After completion of the reaction monitored by TLC, the reaction mixture was filtered through celite and evaporated to a residue. The residue was purified by column chromatography to obtain example 10 as off-white solid (70 mg, 18% yield).

$^1$H-NMR (400 MHz, DMSO-$d_6$): δ=10.33 (s, 1H), 8.93 (s, 2H), 7.99 (m, 2H), 7.69 (d, J=8.4 Hz, 1H), 7.42 (t, J=7.6 Hz, 2H), 7.31 (m, 2H), 5.20 (br, s, 2H), 3.85 (m, 4H), 2.39 (m, 4H), 2.22 (s, 3H).

HPLC-MS: Rt 6.673 m/z 390.5 (MH$^+$).

The following examples were synthesized using the procedure described scheme 7 starting with the corresponding pyridin-2-amine and pyrimidine-5-carboxylic acid derivatives.

Example 11: N-(3-amino-6-phenylpyridin-2-yl)pyrimidine-5-carboxamide $^1$H-NMR (400 MHz, DMSO-$d_6$) δ=10.73 (s, 1H), 9.36 (m, 3H), 7.93 (d, J=7.6 Hz, 2H), 7.72 (d, J=8.0 Hz, 1H), 7.42 (t, J=7.2 Hz, 2H), 7.31 (m, 2H), 5.39 (br, s, 2H).

HPLC-MS: Rt 8.382 m/z 292.2 (MH$^+$).

Example 12: N-(3-amino-6-(4-fluorophenyl)pyridin-2-yl)pyrimidine-5-carboxamide $^1$H-NMR (400 MHz, DMSO-$d_6$) δ=10.72 (s, 1H), 9.36 (d, J=4.8 Hz, 1H), 9.31 (s, 2H), 7.98 (dd, J=14.4, 6.0 Hz, 2H), 7.70 (d, J=8.4 Hz, 1H), 7.25 (m, 3H), 5.39 (br, s, 2H).

HPLC-MS: Rt 11.104 m/z 310.3 (MH$^+$).

Example 13: N-(3-amino-6-(4-fluorophenyl)pyridin-2-yl)-6-(4-methylpiperazin-1-yl)nicotinamide $^1$H-NMR (400 MHz, DMSO-$d_6$) δ=10.35 (s, 1H), 8.96 (s, 2H), 7.95 (d, J=7.6 Hz, 2H), 7.69 (d, J=8.0 Hz, 1H), 7.42 (t, J=7.6 Hz, 2H), 7.29 (m, 2H), 5.21 (br, s, 2H), 3.85 (t, J=4.4 Hz, 4H), 3.69 (t, J=4.4 Hz, 4H).

HPLC-MS: Rt 12.094 m/z 377.3 (MH$^+$).

Example 14: N-(3-amino-6-(4-fluorophenyl)pyridin-2-yl)-2-morpholinopyrimidine-5-carboxamide $^1$H-NMR (400 MHz, DMSO-$d_6$) δ=10.34 (s, 1H), 8.97 (s, 2H), 7.99 (m, 2H), 7.68 (d, J=8.4 Hz, 1H), 7.32 (d, J=8.4 Hz, 1H), 7.27 (t, J=8.8 Hz, 2H), 5.21 (br, s, 2H), 3.85 (t, J=4.4 Hz, 4H), 3.69 (t, J=4.4 Hz, 4H).

HPLC-MS: Rt 12.456 m/z 395.6 (MH$^+$).

Example 15: N-(3-amino-6-(4-fluorophenyl)pyridin-2-yl)-2-(4-methylpiperazin-1-yl)pyrimidine-5-carboxamide $^1$H-NMR (400 MHz, DMSO-$d_6$) δ=10.32 (s, 1H), 8.93 (s, 2H), 7.99 (m, 2H), 7.67 (d, J=8.4 Hz, 1H), 7.25 (t, J=8.8 Hz, 3H), 5.21 (br, s, 2H), 3.86 (m, 4H), 2.44 (m, 4H), 2.24 (s, 3H).

HPLC-MS: Rt 7.205 m/z 408.3 (MH$^+$).

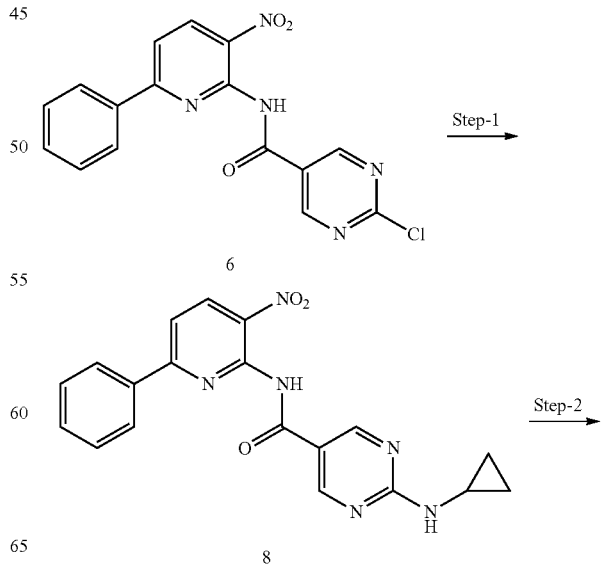

Scheme 8: Synthesis of example 16

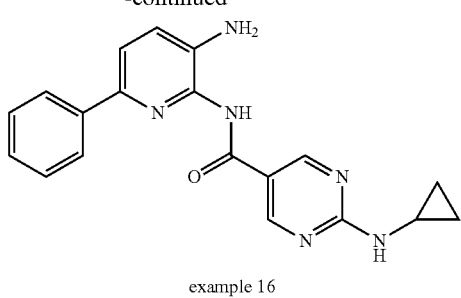

example 16

Step-1: Synthesis of 2-(cyclopropylamino)-N-(3-nitro-6-phenylpyridin-2-yl)pyrimidine-5-carboxamide (Intermediate 8)

To a solution Cyclopropylamine (96.5 mg) in DMF (3 ml) was added DIPEA (327 mg) and Intermediate 6 (300 mg) was heated in seal tube at 110° C. for overnight. After completion of the reaction monitored by TLC, the reaction mixture was diluted with water. The solid precipitated out was collected by filtration to obtain required intermediate 8 as pale yellow solid (300 mg, 93% yield).

15% (w/w)) and allowed reaction to stir for overnight under hydrogen gas (Balloon atm). After completion of the reaction monitored by TLC, the reaction mixture was filtered through celite and evaporated to a residue. The residue was purified by prep-HPLC to obtain example 16 as pale yellow solid (130 mg, 26% yield).

$^1$H-NMR (400 MHz, DMSO-$d_6$): δ=10.26 (s, 1H), 8.89 (br, s, 2H), 8.03 (d, J=4.0 Hz, 1H), 7.99 (m, 2H), 7.66 (d, J=8.4 Hz, 1H), 7.42 (t, J=8.4 Hz, 2H), 7.31 (m, 2H), 5.18 (br, s, 2H), 2.84 (m, 1H), 0.75 (m, 2H), 0.55 (m, 2H).

HPLC-MS: Rt 11.419 m/z 347.1 (MH$^+$).

The following examples were synthesized using the procedure described in scheme 8 starting from the corresponding 2-chloro-N-(3-nitropyridin-2-yl)pyrimidine-5-carboxamide and amine derivatives.

Example 17: N-(3-amino-6-(4-fluorophenyl)pyridin-2-yl)-2-(cyclopropylamino)pyrimidine-5-carboxamide $^1$H-NMR: NMR (400 MHz, DMSO-d6) δ=10.26 (s, 1H), 8.89 (br, s, 2H), 8.03 (d, J=4.0 Hz, 1H), 7.99 (m, 2H), 7.66 (d, J=8.4 Hz, 1H), 7.25 (m, 3H), 5.18 (br, s, 2H), 2.86 (m, 1H), 0.75 (m, 2H), 0.54 (m, 2H).

HPLC-MS: Rt 12.233 m/z 365.1 (MH$^+$).

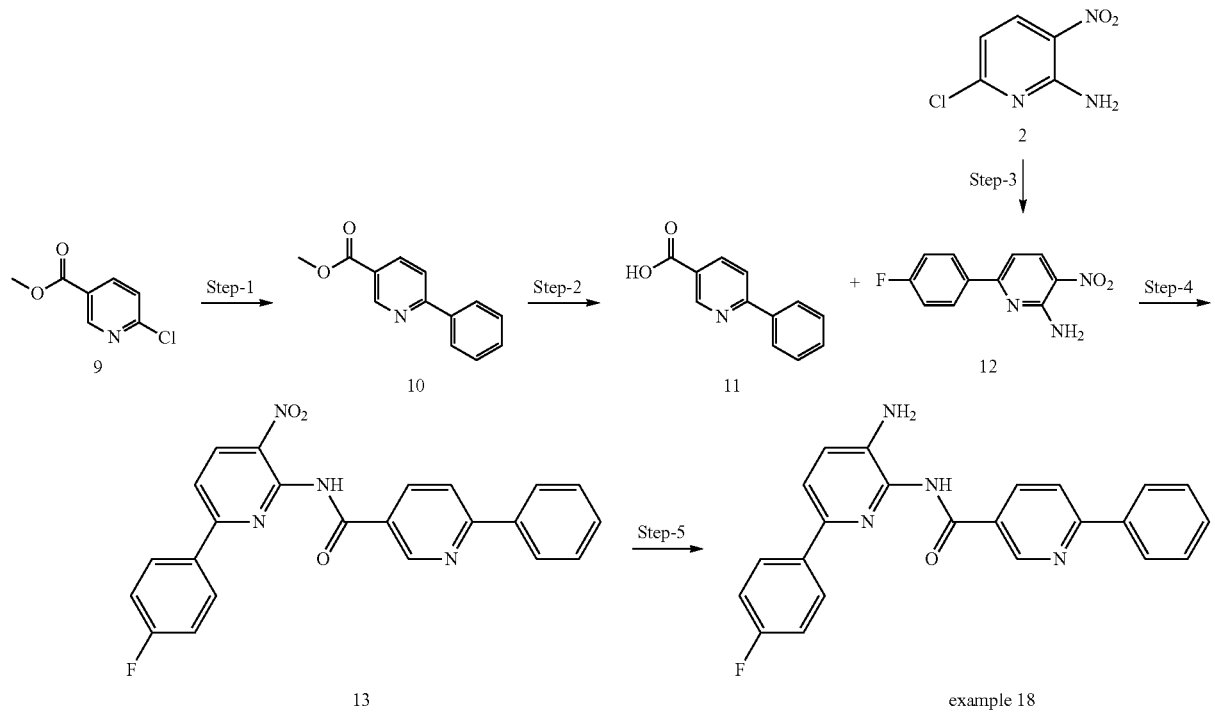

Scheme 9: Synthesis of Example 18

Step-2: Synthesis of N-(3-amino-6-phenylpyridin-2-yl)-2-(cyclopropylamino)pyrimidine-5-carboxamide. Example 16

To a solution intermediate 8 (300 mg) in ethanol (10 ml) and ethyl acetate (50 ml) was added Pd/C (10%) (60 mg,

Step-1: Synthesis of methyl 6-phenylnicotinate (Intermediate 10)

Intermediate 9 (500 mg), Phenyl boronic acid (499 mg), Cs$_2$CO$_3$ (1.52 g), 8 ml 1,4-Dioxane and 0.5 ml water were added to a 3-neck 100 mL round bottom flask. Nitrogen was bubbled directly into the mixture for 20 minutes. Pd(dppf)Cl$_2$·CH$_2$Cl$_2$ (238 mg, 0.1 eq.) was added and the mixture refluxed at 110° C. for 2 h under nitrogen. The reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography and isolated intermediate 10 as an off white solid (606 mg; 94% yield).

Step-2: Synthesis of 6-phenylnicotinic acid (Intermediate 11)

To a solution Intermediate 10 (606 mg) in methanol (30 ml) was added 10% NaOH solution (2.5 ml) and allowed reaction to refluxed at for 70° C. for 3 h. After completion of the reaction monitored by TLC, the reaction mixture was evaporated and made acidic by 2N HCl to get solid which was filtered and dried to obtain intermediate 11 as an off white solid (460 mg, 75% yield).

Step-3: Synthesis of 6-(4-fluorophenyl)-3-nitropyridin-2-amine (Intermediate 12)

Intermediate 2 (700 mg), 4-Fluoro Phenyl boronic acid (788 mg), Cs$_2$CO$_3$ (2.1 g), 50 ml 1,4-Dioxane and 3 ml water were added to a 3-neck 100 ml round bottom flask. Nitrogen was bubbled directly into the mixture for 20 minutes. Pd(dppf)Cl$_2$·CH$_2$Cl$_2$ (328 mg, 0.1 eq.) was added and the mixture refluxed at 110° C. for 2 h under nitrogen. The reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography and isolated intermediate 12 as pale yellow solid (725 mg, 67% yield).

Step-4: Synthesis of N-(6-(4-fluorophenyl)-3-nitropyridin-2-yl)-6-phenylnicotinamide (Intermediate 13)

A solution of intermediate 11 (250 mg) in THF (30 ml), TEA (380.6 mg) and Ethyl chloro formate (339 mg) was added and allowed to stir 1 h at room temperature. The reaction mixture was diluted with water, and the precipitate that formed was filtered and dried to obtain anhydride. A solution of intermediate 12 (234 mg) in THF (30 ml), NaHMDS (1.0M in THF) (3.2 ml) was added slowly at −35° C. and allowed to stir 1 h at same temperature. To this solution, anhydride in THF (5 ml) was added immediately and allowed the reaction mixture warm to room temperature. After completion, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 13 pale yellow solid (230 mg, 58% yield).

Step-5: Synthesis of N-(3-amino-6-(4-fluorophenyl)pyridin-2-yl)-6-phenylnicotinamide. Example 18

To a solution of intermediate 13 (230 mg) in ethanol (12 ml) and ethyl acetate (30 ml) was added Pd/C (10%) (35 mg, 15% (w/w)) and allowed reaction to stir for overnight under hydrogen gas (Balloon atm). After completion of the reaction monitored by TLC, the reaction mixture was filtered through celite and evaporated to a residue. The residue was purified by column chromatography to obtain the desired compound as off-white solid (103 mg, 35% yield).

$^1$H-NMR (400 MHz, DMSO-d$_6$): δ=10.60 (s, 1H), 9.26 (s, 1H), 8.47 (dd, J=10.8, 2.9 Hz, 1H), 8.21 (d, J=8.4 Hz, 2H), 8.16 (d, J=8.4 Hz, 1H), 7.99 (m, 2H), 7.7 (d, J=8.4 Hz, 1H), 7.57 (m, 3H), 7.28 (m, 3H), 5.28 (s, 2H).

HPLC-MS: Rt 16.154 m/z 385.2 (MH$^+$).

The following examples were synthesized using the procedure described in scheme 9 starting from the corresponding pyridin-2-amine and nicotinic acid derivatives.

Example 19: N-(3-amino-6-(4-fluorophenyl)pyridin-2-yl)-6-(4-fluorophenyl)nicotinamide $^1$H-NMR (400 MHz, DMSO-d$_6$) δ=10.60 (s, 1H), 9.25 (s, 1H), 8.47 (dd, J=10.4, 2.4 Hz, 1H), 8.28 (m, 2H), 8.16 (d, J=8.4 Hz, 1H), 7.99 (m, 2H), 7.7 (d, J=8.4 Hz, 1H), 7.39 (m, 2H), 7.28 (m, 3H), 5.28 (s, 2H).

HPLC-MS: Rt 15.831 m/z 403.2 (MH$^+$).

Example 20: N-(3-amino-6-(4-fluorophenyl)pyridin-2-yl)-[2,4'-bipyridine]-5-carboxamide $^1$H-NMR (400 MHz, DMSO-d$_6$) δ=10.66 (s, 1H), 9.31 (s, 1H), 8.76 (d, J=4.4, 2H), 8.54 (d, J=7.6 Hz, 1H), 8.32 (d, J=8.0 Hz, 1H), 8.16 (d, J=4.4 Hz, 2H), 7.96 (m, 2H), 7.7 (d, J=8.4 Hz, 1H), 7.28 (m, 3H), 5.31 (s, 2H).

HPLC-MS: Rt 11.682 m/z 386.1 (MH$^+$).

Example 21: N-(3-amino-6-(4-fluorophenyl)pyridin-2-yl)-[2,3'-bipyridine]-5-carboxamide $^1$H-NMR (400 MHz, DMSO-d$_6$) δ=10.63 (s, 1H), 9.37 (d, J=1.6 Hz, 1H), 9.29 (d, J=1.6 Hz, 1H), 8.70 (dd, J=6.4, 1.6 Hz, 1H), 8.56 (m, 1H), 8.51 (dd, J=10.8, 2.4 Hz, 1H), 8.26 (d, J=8.0 Hz, 1H), 7.99 (m, 2H), 7.70 (d, J=8.4 Hz, 1H), 7.59 (m, 1H), 7.28 (m, 3H), 5.30 (br, s, 2H).

HPLC-MS: Rt 12.080 m/z 385.8 (MH$^+$).

Example 22: N-(3-amino-6-(4-fluorophenyl)pyridin-2-yl)-6-(3-cyanophenyl)nicotinamide $^1$H-NMR (400 MHz, DMSO-d$_6$) δ=10.68 (s, 1H), 9.29 (br, s, 1H), 8.65 (br, s, 1H), 8.57 (m, 2H), 8.32 (d, J=8.0 Hz, 1H), 8.00 (m, 3H), 7.79 (m, 2H), 7.28 (m, 3H), 5.33 (br, s, 2H).

HPLC-MS: Rt 14.559 m/z 410.2 (MH$^+$).

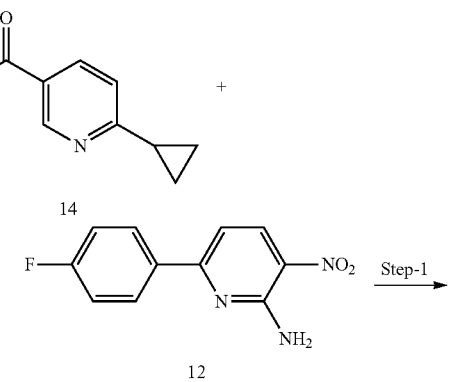

Scheme 10: Synthesis of example 23

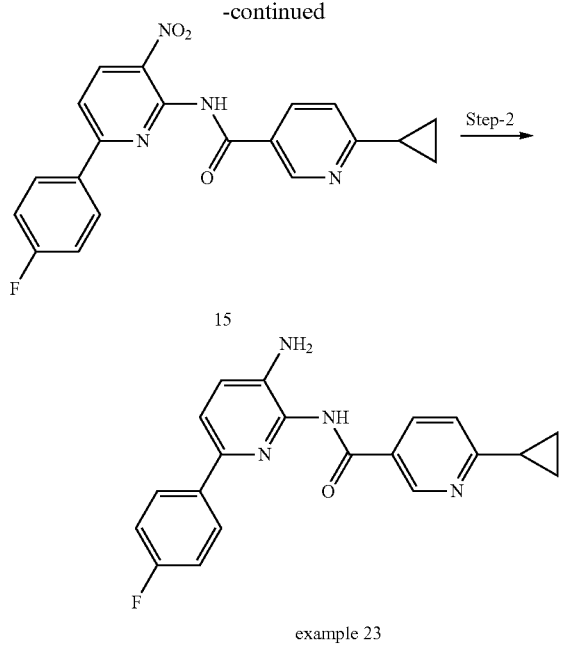

example 23

Step-1: Synthesis of 6-cyclopropyl-N-(6-(4-fluorophenyl)-3-nitropyridin-2-yl)nicotinamide (Intermediate 15)

A solution of intermediate 14 (412 mg) in THF (35 ml), TEA (770.5 mg) and Ethyl chloro formate (686.6 mg) was added and allowed to stir 1 h at room temperature. The reaction mixture was diluted with water, and the precipitate that formed was filtered and dried to obtain anhydride. A solution of intermediate 12 (297 mg) in THF (35 ml), NaHMDS (1.0M in THF) (5 ml) was added slowly at −35° C. and allowed to stir 1 h at same temperature. To this solution, anhydride in THF (5 ml) was added immediately and allowed the reaction mixture warm to room temperature. After completion, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 15 as pale yellow solid (190 mg, 32% yield).

Step-2: Synthesis of N-(3-amino-6-(4-fluorophenyl)pyridin-2-yl)-6-cyclopropylnicotinamide (Example 23)

To a solution intermediate 15 (190 mg) in ethanol (12 ml) and ethyl acetate (30 ml) was added Pd/C (10%) (28.5 mg, 15% (w/w)) and allowed reaction to stir for overnight under hydrogen gas (Balloon atm). After completion of the reaction monitored by TLC, the reaction mixture was filtered through celite and evaporated to a residue. The residue was purified by column chromatography to obtain required compound as pale yellow solid (38 mg, 21% yield).

$^1$H-NMR (400 MHz, DMSO-$d_6$): δ=10.45 (s, 1H), 9.00 (d, J=2.0 Hz, 1H), 8.22 (dd, J=10.8, 2.4 Hz, 1H), 7.98 (m, 2H), 7.67 (d, J=8.0 Hz, 1H), 7.45 (d, J=8.4 Hz, 1H), 7.26 (m, 3H), 5.21 (s, 2H), 2.24 (m, 1H), 1.05 (m, 4H).

HPLC-MS: Rt 13.997 m/z 349.1 (MH$^+$).

The following example was synthesized using the procedure described in scheme 10 starting from the corresponding pyridin-2-amine derivative and 6-cyclopentylnicotinic acid.

Example 24: N-(3-amino-6-(4-fluorophenyl)pyridin-2-yl)-6-cyclopentylnicotinamide $^1$H-NMR (400 MHz, DMSO-$d_6$) δ=10.51 (s, 1H), 9.09 (d, J=2.0 Hz, 1H), 8.26 (dd, J=10.8, 2.4 Hz, 1H), 7.98 (m, 2H), 7.69 (d, J=8.4 Hz, 1H), 7.44 (d, J=8.0 Hz, 1H), 7.26 (m, 3H), 5.25 (s, 2H), 3.3 (m, 1H), 2.04 (m, 3H), 1.80 (m, 6H).

HPLC-MS: Rt 15.746 m/z 424.2 (MH$^+$).

Scheme 11: Synthesis of example 25

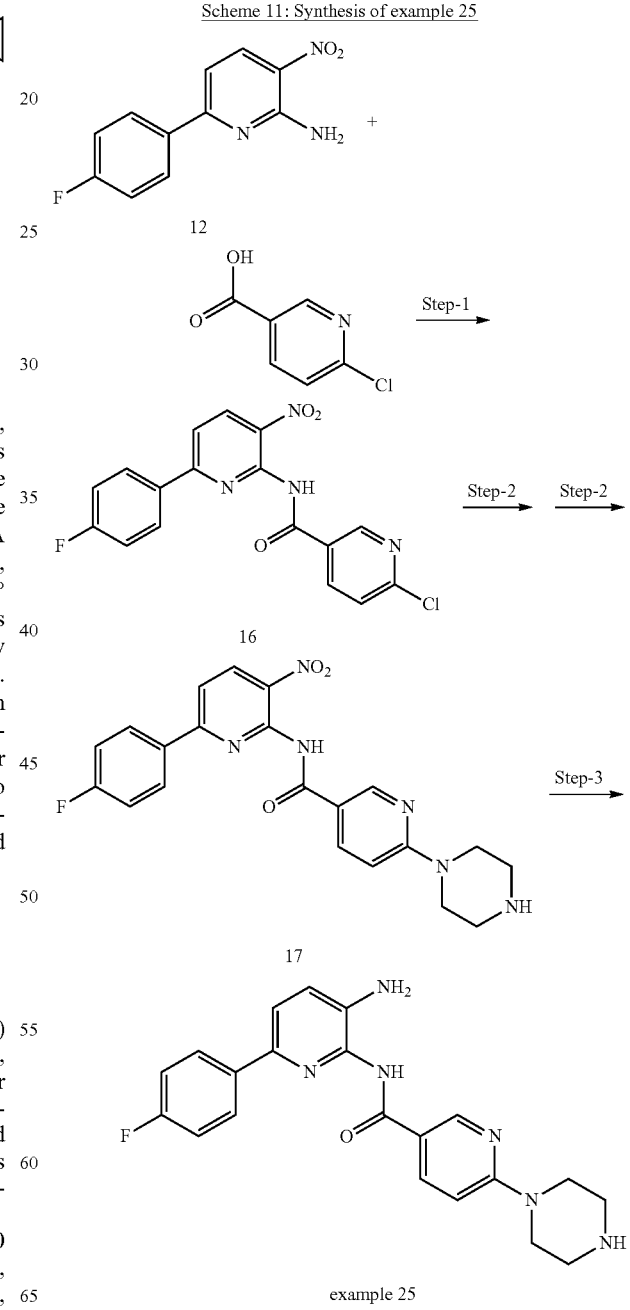

example 25

Step-1: Synthesis of 6-chloro-N-(6-(4-fluorophenyl)-3-nitropyridin-2-yl)nicotinamide (Intermediate 16)

A solution of 6-chloro-3-nicotonic acid (430 mg) in THF (30 ml), TEA (830 mg) and Ethyl chloro formate (739 mg) was added and allowed to stir 1 h at room temperature. The reaction mixture was diluted with water, and the precipitate that formed was filtered and dried to obtain anhydride. A solution of intermediate 12 (510 mg) in THF (30 ml), NaHMDS (6.8 ml) was added slowly at −35° C. and allowed to stir 1 h at same temperature. To this solution, anhydride in THF (5 ml) was added immediately and allowed the reaction mixture warm to room temperature. After completion, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 16 (665 mg, 78% yield).

Step-2: Synthesis of N-(6-(4-fluorophenyl)-3-nitropyridin-2-yl)-6-(piperazin-1-yl)nicotinamide (intermediate 17)

To a solution piperazine (207.5 mg) in DMSO (4 ml) was added DIPEA (622.5 mg) and intermediate 16 (300 mg) was heated in seal tube at 110° C. for overnight. After completion of the reaction monitored by TLC, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 17 as a pale brown semi solid (142 mg, 28% yield).

Step-3: Synthesis of N-(3-amino-6-(4-fluorophenyl)pyridin-2-yl)-6-(piperazin-1-yl)nicotinamide (Example 25)

To a solution intermediate 17 (142 mg) in ethanol (12 ml) and ethyl acetate (24 ml) was added Pd/C (10%) (22.0 mg, 15% (w/w)) and allowed reaction to stir for overnight under hydrogen gas (Balloon atm). After completion of the reaction monitored by TLC, the reaction mixture was filtered through celite and evaporated to a residue. The residue was purified by column chromatography to obtain required compound as a brown solid (26 mg, 20% yield).

$^1$H-NMR (400 MHz, DMSO-d$_6$): δ=10.20 (br, s, 1H), 8.75 (d, J=2.0 Hz, 1H), 8.1 (dd, J=11.2, 2.0 Hz, 1H), 7.96 (m, 2H), 7.63 (d, J=8.4 Hz, 1H), 7.2 (m, 3H), 6.85 (d, J=8.8 Hz, 1H), 5.11 (br, s, 2H), 3.54 (m, 4H), 2.75 (m, 4H), 1.95 (s, 1H).

HPLC-MS: Rt 8.070 m/z 393.2 (MH$^+$).

The following example was synthesized using the procedure described in scheme 11 starting from the corresponding pyrimidin-2-amine and nicotinic acid derivatives.

Example 26: N-(5-amino-2-(4-fluorophenyl)pyrimidin-4-yl)-6-(piperazin-1-yl)nicotinamide $^1$H-NMR (400 MHz, DMSO-d$_6$) δ=10.56 (s, 1H), 8.78 (d, J=2.4 Hz, 1H), 8.36 (s, 1H), 8.28 (m, 2H), 8.13 (dd, J=11.2, 2.4 Hz, 1H), 7.29 (m, 2H), 6.90 (d, J=8.8 Hz, 1H), 5.29 (br, s, 2H), 3.60 (m, 4H), 2.79 (m, 4H). (—NH missing).

HPLC-MS: Rt 8.120 m/z 394.2 (MH$^+$).

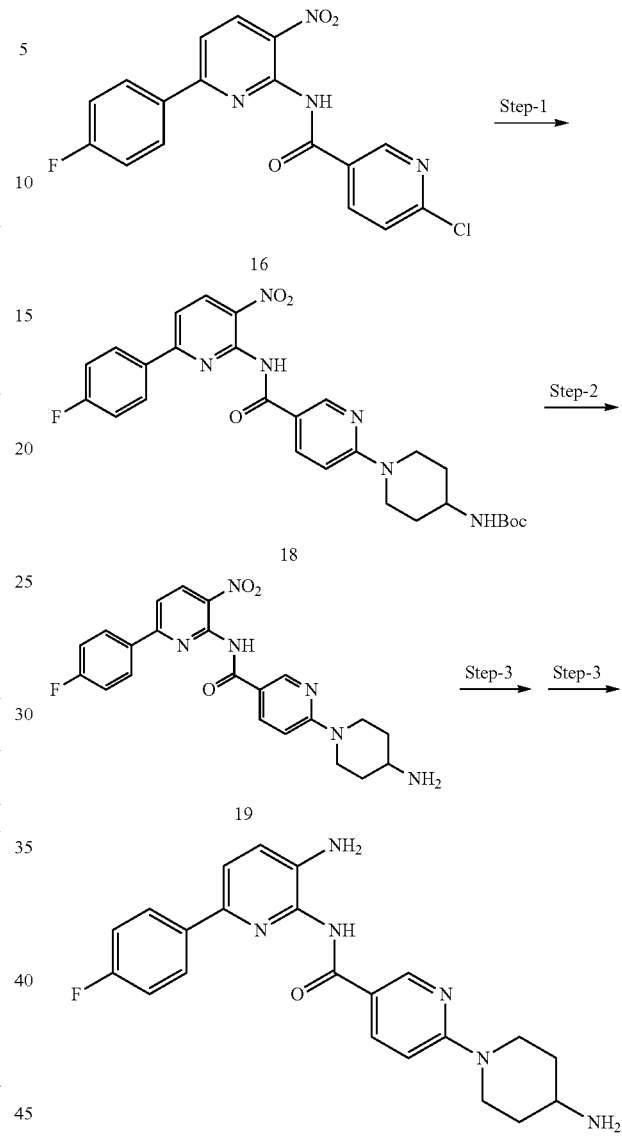

Scheme 12: Synthesis of example 27

Step-1: Synthesis of tert-butyl (1-(5-((6-(4-fluorophenyl)-3-nitropyridin-2-yl)carbamoyl)pyridin-2-yl)piperidin-4-yl)carbamate (Intermediate 18)

To a solution tert-butyl piperidin-4-ylcarbamate (469 mg) in DMSO (5 ml) was added DIPEA (726.2 mg) and intermediate 16 (350 mg) was heated in seal tube at 110° C. for overnight. After completion of the reaction monitored by TLC, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 18 as pale brown semi solid (400 mg, 64% yield).

Step-2: Synthesis of 6-(4-aminopiperidin-1-yl)-N-(6-(4-fluorophenyl)-3-nitropyridin-2-yl)nicotinamide (intermediate 19)

To a solution intermediate 18 (390 mg) in DCM (12 ml) was added TFA (3 ml) at 0° C. and allowed reaction to stir at room temperature for 3 h under nitrogen. After completion of the reaction monitored by TLC, the reaction mixture was basified (PH~8) with sodium hydrogen carbonate and evaporated to a residue to obtain required intermediate 19 as a brown solid (390 mg, 98% yield).

Step-3: Synthesis of N-(3-amino-6-(4-fluorophenyl)pyridin-2-yl)-6-(4-aminopiperidin-1-yl)nicotinamide (Example 27)

To a solution intermediate 19 (319 mg) in ethanol (12 ml) and ethyl acetate (25 ml) was added Pd/C (10%) (47.8 mg, 15% (w/w)) and allowed reaction to stir for overnight under hydrogen gas (Balloon atm). After completion of the reaction monitored by TLC, the reaction mixture was filtered through celite and evaporated to a residue. The residue was purified by column chromatography to obtain required compound as pale brown solid (140 mg, 46% yield).

$^1$H-NMR (400 MHz, DMSO-d$_6$): δ=10.33 (s, 1H), 8.87 (d, J=2.4 Hz, 1H), 8.24 (dd, J=11.2, 2.4 Hz, 1H), 8.09 (br, s, 2H), 8.06 (m, 2H), 7.73 (d, J=8.4 Hz, 1H), 7.33 (m, 2H), 7.04 (d, J=9.2 Hz, 1H), 5.21 (br, s, 2H), 4.57 (d, J=13.6 Hz, 2H), 3.10 (t, J=11.6 Hz, 2H), 2.2 (d, J=10.0 Hz, 2H), 1.55 (m, 2H).

HPLC-MS: Rt 7.974 m/z 407.2 (MH$^+$).

The following example was synthesized using the procedure described in scheme 12 starting from the corresponding pyrimidin-2-amine and nicotinic acid derivatives.

Example 28: N-(5-amino-2-(4-fluorophenyl)pyrimidin-4-yl)-6-(4-aminopiperidin-1-yl)nicotinamide $^1$H-NMR (400 MHz, DMSO-d$_6$) δ=8.74 (d, J=2.0 Hz, 1H), 8.33 (s, 1H), 8.25 (m, 2H), 8.08 (dd, J=11.2, 2.4 Hz, 1H), 7.26 (m, 2H), 6.89 (d, J=9.2 Hz, 1H), 5.25 (br, s, 2H), 4.31 (d, J=13.2 Hz, 2H), 3.03 (m, 2H), 2.89 (m, 1H), 1.82 (m, 2H), 1.19 (m, 2H). (—NH and —NH$_2$ missing).

HPLC-MS: Rt 8.144 m/z 408.2 (MH$^+$).

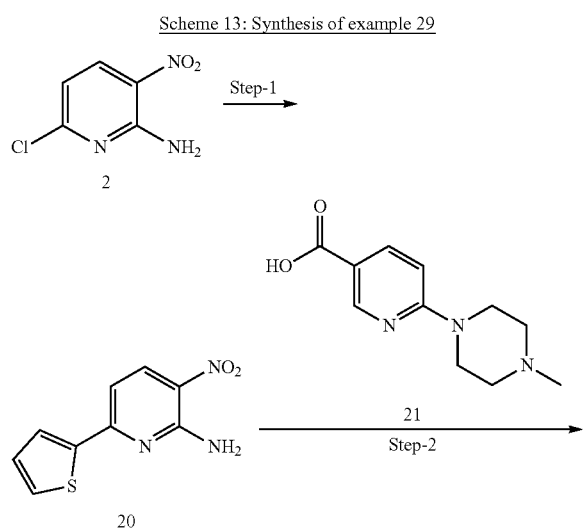

Scheme 13: Synthesis of example 29

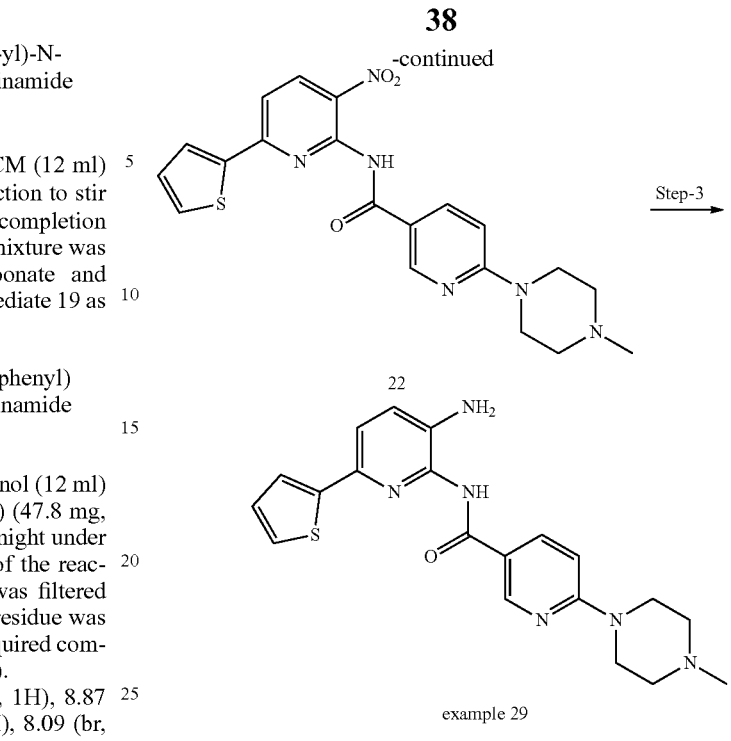

example 29

Step-1: Synthesis of 3-nitro-6-(thiophen-2-yl)pyridin-2-amine (Intermediate 20)

Intermediate 2 (600 mg), Thiophene-2-boronic acid (533 mg), Cs$_2$CO$_3$ (1.8 g), 10 ml 1,4-Dioxane and 2 ml water were added to a 3-neck 100 mL round bottom flask. Nitrogen was bubbled directly into the mixture for 20 minutes. Pd(dppf)Cl$_2$.CH$_2$Cl$_2$ (140 mg) was added and the mixture refluxed at 110° C. for 3 h under nitrogen. The reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography and isolated intermediate 20 as off white solid (300 mg, 78% yield).

Step-2: Synthesis of 6-(4-methylpiperazin-1-yl)-N-(3-nitro-6-(thiophen-2-yl)pyridin-2-yl)nicotinamide (Intermediate 22)

A solution of intermediate 21 (597 mg) in DMF (30 ml), DIPEA (435 mg) and TBTU (953 mg) was added and allowed to stir 1 h at room temperature. The reaction mixture was diluted with water, and the precipitate that formed was filtered and dried to obtain anhydride. A solution of intermediate 20 (300 mg) in THF (50 ml), NaHMDS (2.7 ml) was added slowly at −35° C. and allowed to stir 1 h at the same temperature. To this solution, anhydride in THF (5 ml) was added immediately and allowed the reaction mixture warm to room temperature. After completion, the reaction mixture was diluted with ethyl acetate/water. The layers were separated and the aqueous layer was extracted with ethyl acetate. The organic layer was dried over magnesium sulfate, filtered and evaporated to a residue. The residue was purified by column chromatography to obtain required intermediate 22 as yellow solid (400 mg, 72% yield).

Step-3: Synthesis of N-(3-amino-6-(thiophen-2-yl)pyridin-2-yl)-6-(4-methylpiperazin-1-yl)nicotinamide. Example 29

To a solution intermediate 22 (200 mg) in methanol/ethanol (20/3 ml) and THF/ethyl acetate (9/9 ml) was added Pd/C (10%) (40 mg, 20% (w/w)) and allowed reaction to stir for overnight under hydrogen gas (Balloon atm). After completion of the reaction monitored by TLC, the reaction mixture was filtered through celite and evaporated to a residue. The residue was purified by column chromatography to obtain required compound as pale orange solid (25 mg, 13% yield).

$^1$H-NMR (400 MHz, DMSO-$d_6$): δ=10.23 (s, 1H), 8.79 (d, J=2.4 Hz, 1H), 8.15 (dd, J=11.6, 2.4 Hz, 1H), 7.61 (d, J=8.4 Hz, 1H), 7.52 (dd, J=4.8, 1.2 Hz, 1H), 7.44 (dd, J=6.0, 1.2 Hz, 1H), 7.22 (d, J=8.0 Hz, 1H), 7.08 (m, 1H), 6.92 (d, J=9.2 Hz, 1H), 5.13 (br, s, 2H), 3.65 (t, J=4.4 Hz, 4H), 2.40 (t, J=4.8 Hz, 4H), 2.22 (s, 3H).

HPLC-MS: Rt 8.778 m/z 395.1 (MH$^+$).

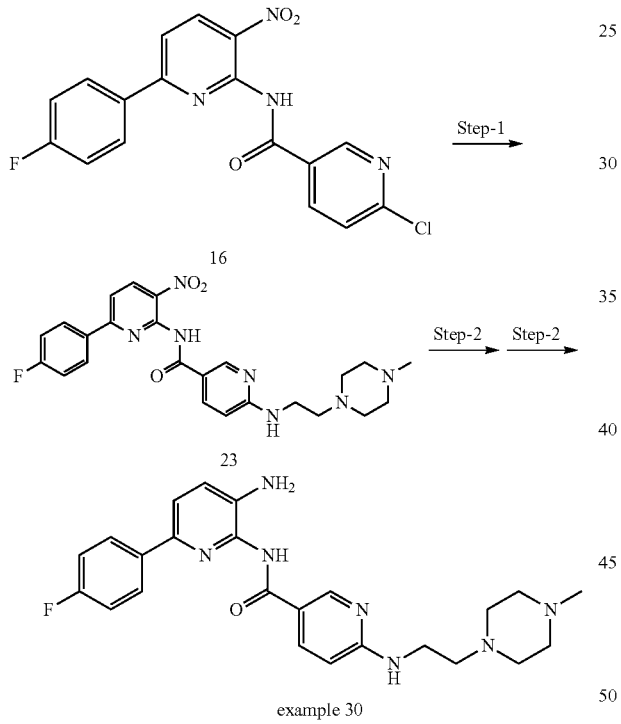

Scheme 14: Synthesis of example 30 example 30

Step-1: Synthesis of N-(6-(4-fluorophenyl)-3-nitropyridin-2-yl)-6-((2-(4-methylpiperazin-1-yl)ethyl)amino)nicotinamide (Intermediate 23)

To a solution of intermediate 16 (500 mg) in DMSO (20 ml) and DIPEA (1.44 ml, 6 eq.) was added 2-(4-Methylpiperazin-1-yl)-ethyl-diazene (400 mg) and then allowed reaction to heat at 110° C. for 16 h. After this time, the reaction mixture was diluted with water and added ethyl acetate. The layers were separated and the aqueous layer was extracted with ethyl acetate. The organic layer was dried over magnesium sulfate, filtered and evaporated to a residue. The residue was purified by column chromatography to obtain required intermediate 23 (250 mg, 42% yield).

Step-2: Synthesis of N-(3-amino-6-(4-fluorophenyl)pyridin-2-yl)-6-((2-(4-methylpiperazin-1-yl)ethyl)amino)nicotinamide (Example 30)

To a solution intermediate 23 (240 mg) in ethanol (7.5 ml) and water (2.5 ml) was added Fe (112 mg) and NH$_4$Cl (215 mg), allowed reaction to heat at 90° C. for 1 h. After completion of the reaction monitored by TLC, the reaction mixture was filtered through celite and evaporated to a residue. The residue was purified by prep HPLC to obtain required compound as pale yellow solid (21 mg, 10% yield).

$^1$H-NMR (400 MHz, DMSO-$d_6$): δ=10.12 (s, 1H), 8.71 (d, J=2.4 Hz, 1H), 8.00 (m, 3H), 7.65 (d, J=8.4 Hz, 1H), 7.26 (m, 3H), 7.05 (br, 1H), 6.55 (d, J=8.8 Hz, 1H), 5.11 (br, s, 2H), 3.45 (m, 2H), 2.67 (m, 3H), 2.33 (m, 5H), 2.18 (s, 3H).

HPLC-MS: Rt 8.684 m/z 450.2 (MH$^+$).

The following example was synthesized using the procedure described in scheme 14 starting from the corresponding 2-chloro-N-(3-nitropyridin-2-yl)pyrimidine-5-carboxamide and amine derivatives.

Example 31: N-(3-amino-6-(4-fluorophenyl)pyridin-2-yl)-6-((2-(pyridin-3-yl)ethyl)amino) nicotinamide $^1$H-NMR (400 MHz, DMSO-$d_6$) δ=10.13 (s, 1H), 8.73 (d, J=2.0 Hz, 1H), 8.47 (br, s, 1H), 8.42 (d, J=4.0 Hz, 1H), 8.00 (m, 2H), 7.69 (m, 2H), 7.34 (m, 2H), 7.26 (m, 2H), 6.53 (d, J=8.8 Hz, 1H), 5.12 (br, s, 2H), 3.61 (m, 4H), 2.91 (br, s, 2H).

HPLC-MS: Rt 9.725 m/z 429.1 (MH$^+$).

The invention claimed is:
1. A compound of formula (I):

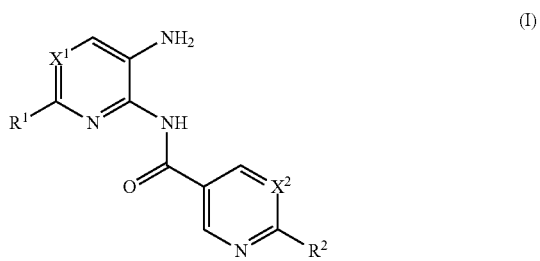

wherein:
$X^1$ and $X^2$ represent, independently, CH or N;
$R^1$ represents:
  a) phenyl group optionally substituted by one or more substituents selected from the group consisting of halogen atom, linear or branched $C_1$-$C_4$ haloalkyl group, and linear or branched alkoxy,
  b) five or a six-membered heteroaryl ring optionally substituted by one or more substituents selected from the group consisting of halogen atom, linear or branched $C_1$-$C_4$ alkoxy, cyano group, linear or branched $C_1$-$C_4$ haloalkyl, linear or branched $C_1$-$C_3$ alkyl, $C_3$-$C_6$ cycloalkyl, $C_3$-$C_6$ cycloalkoxy and $C_5$-$C_6$ heterocyclic ring optionally substituted by one or more halogen atoms;
$R^2$ represents:
  a) —N($R^3$)($R^4$) group, wherein:
    $R^3$ and $R^4$ form together with the nitrogen atom to which they are bound a five or six-membered saturated heterocycle comprising optionally an additional heteroatom as part of the cycle selected from N and O, which is optionally substituted by a $C_1$-$C_3$ alkyl group or an —N($R^5$)($R^6$) group, wherein $R^5$ and $R^6$ form together with the nitrogen atom to which they are bound a five or six-membered saturated heterocycle comprising optionally an additional heteroatom as part of the cycle selected from N and O, which is optionally substituted by a $C_1$-$C_3$ alkyl group, or $R^3$ and $R^4$ represent independently a group selected from hydrogen atom, $C_3$-$C_6$ cycloalkyl group and linear or branched $C_1$-$C_3$ alkyl, which is optionally substituted by a five or six-membered heterocycle comprising one or two heteroatoms as part of the cycle selected from N and O, which is optionally substituted by linear or branched $C_1$-$C_3$ alkyl group,
- b) phenyl ring optionally substituted by one or more substituent selected from halogen atoms and cyano group,
- c) $C_3$-$C_6$ cycloalkyl optionally substituted by one or more substituent selected from linear or branched $C_1$-$C_3$ alkyl and hydroxy group,
- d) $C_5$-$C_6$ heteroaryl optionally substituted by a group selected from halogen atom, linear or branched $C_1$-$C_3$ alkyl and linear or branched $C_1$-$C_4$ alkoxy and —N($R^5$)($R^6$) group, wherein $R^5$ and $R^6$ form together with the nitrogen atom to which they are bound a five or six-membered saturated cycle comprising optionally an additional heteroatom selected from N and O as part of the cycle, which is optionally substituted by a $C_1$-$C_3$ alkyl group, or
- e) hydrogen atom, or pharmaceutically acceptable salts thereof.

2. The compound according to claim 1 wherein $x^1$ and $X^2$ are —CH groups.

3. The compound according to claim 2 wherein $R^1$ represents a phenyl group optionally substituted by one or more halogen atom.

4. The compound according to claim 3 wherein $R^2$ represents a —N($R^3$)($R^4$) group wherein $R^3$ and $R^4$ form together with the nitrogen atom to which they are bound a five or six-membered saturated heterocycle comprising optionally an additional heteroatom selected from N and O as part of the cycle, which heterocycle is optionally substituted by a $C_1$-$C_3$ alkyl group or an —N($R^5$)($R^6$) group.

5. The compound according to claim 4 wherein $R^2$ represents piperazinyl, piperidinyl or morpholinyl ring optionally substituted by a $C_1$-$C_3$ alkyl group or an —N($R^5$)($R^6$) group.

6. The compound according to claim 1 wherein $R^1$ represents a five or a six-membered heteroaryl ring optionally substituted by one or more substituents selected from the group consisting of cyano group, halogen atom and linear or branched $C_1$-$C_4$ haloalkyl.

7. The compound according to claim 1 wherein $R^2$ represents a —N($R^3$)($R^4$) group, wherein $R^3$ and $R^4$ represent independently a group selected from hydrogen atom, $C_3$-$C_6$ cycloalkyl group and $C_1$-$C_3$ alkyl linear or branched, which is optionally substituted by a 5 or 6-membered saturated heterocycle comprising one or two N atom, which heterocycle is optionally substituted by a $C_1$-$C_3$ alkyl group.

8. The compound according to claim 1 wherein $R^2$ represents a phenyl ring optionally substituted by one or more selected from halogen atoms and cyano group.

9. The compound according to claim 1 wherein $R^2$ represents a $C_5$-$C_6$ heteroaryl optionally substituted by one or more substituents selected from halogen atoms and cyano group.

10. The compound according to claim 1 wherein $X^1$ and $X^2$ are —CH groups, $R^1$ represents a phenyl group optionally substituted by one or more halogen atoms, and $R^2$ represents —N($R^3$)($R^4$) group wherein $R^3$ and $R^4$ form together with the nitrogen atom to which they are bound a 6 membered heterocycle comprising optionally a heteroatom selected from N and O, which is optionally substituted by a $C_1$-$C_3$ alkyl group or an —N($R^5$)($R^6$) group.

11. The compound according to claim 10, wherein $R^2$ represents a piperazinyl ring optionally substituted by a $C_1$-$C_3$ alkyl group.

12. The compound according to claim 1 which is one of:
N-(3-amino-6-phenylpyridin-2-yl)-6-(4-methylpiperazin-1-yl)nicotinamide
N-(3-amino-6-phenylpyridin-2-yl)nicotinamide
N-(3-amino-6-(4-fluorophenyl)pyridin-2-yl)nicotinamide
N-(3-amino-6-phenylpyridin-2-yl)-6-morpholinonicotinamide
N-(3-amino-6-(4-fluorophenyl)pyridin-2-yl)-6-morpholinonicotinamide
N-(3-amino-6-(4-fluorophenyl)pyridin-2-yl)-6-(4-methylpiperazin-1-yl)nicotinamide
N-(3-amino-6-(4-methoxyphenyl)pyridin-2-yl)-6-(4-methylpiperazin-1-yl)nicotinamide
N-(5-amino-[2,4'-bipyridin]-6-yl)-6-(4-methylpiperazin-1-yl)nicotinamide
N-(3-amino-6-(3,4-difluorophenyl)pyridin-2-yl)-6-(4-methylpiperazin-1-yl)nicotinamide
N-(3-amino-6-phenylpyridin-2-yl)-2-(4-methylpiperazin-1-yl)pyrimidine-5-carboxamide
N-(3-amino-6-phenylpyridin-2-yl)pyrimidine-5-carboxamide
N-(3-amino-6-(4-fluorophenyl)pyridin-2-yl)pyrimidine-5-carboxamide
N-(3-amino-6-(4-fluorophenyl)pyridin-2-yl)-6-(4-methylpiperazin-1-yl)nicotinamide
N-(3-amino-6-(4-fluorophenyl)pyridin-2-yl)-2-morpholinopyrimidine-5-carboxamide
N-(3-amino-6-(4-fluorophenyl)pyridin-2-yl)-2-(4-methylpiperazin-1-yl)pyrimidine-5-carboxamide
N-(3-amino-6-phenylpyridin-2-yl)-2-(cyclopropylamino)pyrimidine-5-carboxamide
N-(3-amino-6-(4-fluorophenyl)pyridin-2-yl)-2-(cyclopropylamino)pyrimidine-5-carboxamide
N-(3-amino-6-(4-fluorophenyl)pyridin-2-yl)-6-phenylnicotinamide
N-(3-amino-6-(4-fluorophenyl)pyridin-2-yl)-6-(4-fluorophenyl)nicotinamide
N-(3-amino-6-(4-fluorophenyl)pyridin-2-yl)-[2,4'-bipyridine]-5-carboxamide
N-(3-amino-6-(4-fluorophenyl)pyridin-2-yl)-[2,3'-bipyridine]-5-carboxamide
N-(3-amino-6-(4-fluorophenyl)pyridin-2-yl)-6-(3-cyanophenyl)nicotinamide
N-(3-amino-6-(4-fluorophenyl)pyridin-2-yl)-6-cyclopropylnicotinamide
N-(3-amino-6-(4-fluorophenyl)pyridin-2-yl)-6-cyclopentylnicotinamide
N-(3-amino-6-(4-fluorophenyl)pyridin-2-yl)-6-(piperazin-1-yl)nicotinamide
N-(5-amino-2-(4-fluorophenyl)pyrimidin-4-yl)-6-(piperazin-1-yl)nicotinamide N-(3-amino-6-(4-fluorophenyl)pyridin-2-yl)-6-(4-aminopiperidin-1-yl)nicotinamide N-(5-amino-2-(4-fluorophenyl)pyrimidin-4-yl)-6-(4-aminopiperidin-1-yl)nicotinamide N-(3-amino-6-(thiophen-2-yl)pyridin-2-yl)-6-(4-methylpiperazin-1-yl)nicotinamide N-(3-amino-6-(4-fluorophenyl)pyridin-2-yl)-6-((2-(4-methylpiperazin-1-yl)ethyl)amino)nicotinamide N-(3-amino-6-(4-fluorophenyl)pyridin-2-yl)-6-((2-(pyridin-3-yl)ethyl)amino)nicotinamide, or a pharmaceutically acceptable salt thereof.

13. A method of treatment of a disease or pathological condition selected from the group consisting of cancer, T-cell malignancies, neurodegenerative diseases, infectious diseases, inflammatory diseases, heart failure, cardiac hypertrophy, diabetes, polycystic kidney disease, sickle cell disease and β-thalassemia disease comprising the administration to a subject in need thereof of an effective amount of a compound as defined in claim 1.

14. A pharmaceutical composition comprising a compound as defined in claim 1, a pharmaceutically acceptable diluent or carrier and optionally a therapeutically effective amount of one or more further therapeutic agents selected from the group consisting of chemotherapeutics agents, anti-inflammatory agents, steroids, immunosuppressants, and therapeutic antibodies.

15. A combination product comprising a compound according to claim 1 and at least a therapeutic agent selected from the group consisting of chemotherapeutics agents, anti-inflammatory agents, steroids, immunosuppressants, immunotherapeutic agents, therapeutic antibodies, adenosine antagonists, Carboplatin, Carmustine (BCNU), Cisplatin, Cyclophosphamide, Etoposide, Irinotecan, Lomustine (CCNU), Methotrexate, Procarbazine, Temozolomide, and Vincristine.

16. The compound according to claim 7, wherein $R^3$ represents linear $C_1$-$C_3$ alkyl substituted by a 5 or 6-membered saturated heterocycle comprising one or two N atom, which is optionally substituted by a $C_1$-$C_3$ alkyl group; and $R^4$ is a hydrogen atom.

17. A pharmaceutical composition comprising a compound as defined according to claim 1 and a pharmaceutically acceptable diluent or carrier.

18. A pharmaceutical composition comprising a compound as defined according to claim 7 and a pharmaceutically acceptable diluent or carrier.

19. A pharmaceutical composition comprising a compound as defined according to claim 16 and a pharmaceutically acceptable diluent or carrier.

20. A pharmaceutical composition comprising a compound as defined according to claim 12 and a pharmaceutically acceptable diluent or carrier.

21. The method according to claim 13 wherein the disease or pathological condition selected from the group consisting of colon cancer, lung cancer, breast cancer, meningioma, neuroblastoma, glioblastoma, medullo blastoma, glioma, astrocytomas, oligodendrogliomas, ependymomas, gangliogliomas, neurilemmomas (Schwannomas), craniopharyngiomas, uterine cervical cancer, pancreatic adenocarcinoma, hepatocellular carcinoma, gastric cancer, tissue cancer, acute myeloid leukemia, acute lymphoblastic leukemia, cutaneous T-cell lymphoma, peripheral T-cell lymphoma, B-cell lymphoma, multiple myeloma, Alzheimer's disease, post-traumatic stress disorder, drug addiction, Parkinson's disease, Huntington's disease, Amyloid-β (Aβ) toxicity, Friedreich's ataxia, myotonic dystrophy, spinal muscular atrophy, fragile X syndrome, a spinocerebellar ataxia, Kennedy's disease, amyotrophic lateral sclerosis, Niemann Pick, Pitt Hopkins, spinal and bulbar muscular atrophy.

22. The combination product according to claim 15 wherein the at least one therapeutic agent is selected from the group consisting of antibodies anti-CTLA4, antibodies anti-PD1, and antibodies anti-PDL1.

23. The combination product according to claim 22 wherein the antibodies are selected from the group consisting of ipilimumab, tremelimumab, nivolumab, pembrolizumab, pidilizumab, atezolizumab and durvalumab.

* * * * *